(12) United States Patent
Ben Haim et al.

(10) Patent No.: US 10,088,436 B2
(45) Date of Patent: Oct. 2, 2018

(54) OBJECT PROCESSING STATE SENSING USING RF RADIATION

(75) Inventors: Yuval Ben Haim, Hod Ha'Sharon (IL); Maksim Berezin, Netanya (IL); Sharon Hadad, Giv'ataim (IL); Avner Libman, Holon (IL); Amichai Ron, Jerusalem (IL); Elliad Silcoff, Tel Aviv (IL); Igal Yaari, Palo Alto, CA (US)

(73) Assignee: GOJI LTD., Hamilton (BM)

( * ) Notice: Subject to any disclaimer, the term of this patent is extended or adjusted under 35 U.S.C. 154(b) by 461 days.

(21) Appl. No.: 14/241,583

(22) PCT Filed: Aug. 30, 2012

(86) PCT No.: PCT/US2012/053044
§ 371 (c)(1),
(2), (4) Date: May 19, 2014

(87) PCT Pub. No.: WO2013/033330
PCT Pub. Date: Mar. 7, 2013

(65) Prior Publication Data
US 2014/0247060 A1    Sep. 4, 2014

Related U.S. Application Data

(60) Provisional application No. 61/612,961, filed on Mar. 19, 2012, provisional application No. 61/529,361, filed on Aug. 31, 2011.

(51) Int. Cl.
*G01N 22/00*    (2006.01)
*H05B 6/64*    (2006.01)
(Continued)

(52) U.S. Cl.
CPC ............. *G01N 22/00* (2013.01); *G01N 27/00* (2013.01); *G01N 27/04* (2013.01); *G06F 15/00* (2013.01);
(Continued)

(58) Field of Classification Search
CPC .................. F26B 3/347; F26B 11/0495; D06F 2058/289; D06F 2058/2806; D06F 58/266;
(Continued)

(56) References Cited

U.S. PATENT DOCUMENTS 3,192,642 A    7/1965    Hughes
3,439,431 A    4/1969    Heidtmann
(Continued)

FOREIGN PATENT DOCUMENTS

DE    2719588    11/1977
DE    102004014338 A1    10/2004
(Continued)

OTHER PUBLICATIONS

Office Action in U.S. Appl. No. 13/599,472, dated Jul. 9, 2015.
(Continued)

*Primary Examiner* — Christopher Kim
(74) *Attorney, Agent, or Firm* — Greenblum & Bernstein, P.L.C.

(57) ABSTRACT

A method for applying RF energy to detect a processing state of an object placed in an energy application zone, during processing of the object, may include applying RF energy to the object during processing. The method may also include receiving computed RF feedback, correlated with one or more processing states of the object; and monitoring the computed RF feedback during the processing to detect the one or more processing states of the object.

35 Claims, 13 Drawing Sheets

(51) Int. Cl.
　　　*G01N 27/00*　　　(2006.01)
　　　*G06F 15/00*　　　(2006.01)
　　　*H05B 6/70*　　　(2006.01)
　　　*G01N 27/04*　　　(2006.01)
　　　*H05B 6/68*　　　(2006.01)

(52) U.S. Cl.
　　　CPC ........... *H05B 6/6441* (2013.01); *H05B 6/688* (2013.01); *H05B 6/705* (2013.01); *Y02B 40/143* (2013.01)

(58) Field of Classification Search
　　　CPC .. D06F 58/28; H05B 6/70; H05B 6/72; H05B 6/6402; H05B 6/80; H05B 6/6408; H05B 6/6441; H05B 6/688; H05B 6/705; H05B 6/76; G01N 22/00; G01N 27/00; G01N 27/04; G06F 15/00; Y02B 40/143
　　　USPC ....... 219/629, 630, 631, 632, 635, 643, 682, 219/690–697, 702, 728–731, 746–750, 219/762; 34/245, 248, 250, 255, 259, 34/260, 261; 426/107, 114, 234
　　　See application file for complete search history.

(56) References Cited

U.S. PATENT DOCUMENTS

| | | | |
|---|---|---|---|
| 4,196,332 A | 4/1980 | MacKay |
| 4,210,795 A | 7/1980 | Lentz |
| 4,297,557 A | 10/1981 | Tyler et al. |
| 4,340,796 A | 7/1982 | Yamaguchi et al. |
| 4,350,858 A | 9/1982 | Yoshida |
| 4,381,439 A | 4/1983 | Miyazawa et al. |
| 4,447,693 A | 5/1984 | Buck |
| 4,475,024 A | 10/1984 | Tateda |
| 4,714,812 A | 12/1987 | Haagensen et al. |
| 5,616,268 A | 4/1997 | Carr |
| 6,222,170 B1 | 4/2001 | Tucker |
| 8,207,479 B2 | 6/2012 | Ben-Shmuel et al. |
| 8,240,914 B1 | 8/2012 | Chapman et al. |
| 8,348,504 B2 | 1/2013 | Gregory et al. |
| 8,839,527 B2 | 9/2014 | Ben-Shmuel et al. |
| 2002/0027135 A1 | 3/2002 | Fagrell et al. |
| 2004/0058706 A1 | 3/2004 | Williamson |
| 2007/0265523 A1 | 11/2007 | Pahlsson et al. |
| 2009/0045191 A1 | 2/2009 | Ben-Shmuel et al. |
| 2009/0057302 A1 | 3/2009 | Ben-Shmuel et al. |
| 2009/0188396 A1 | 7/2009 | Hofmann et al. |
| 2009/0236334 A1* | 9/2009 | Ben-Shmuel ...... B65D 81/3453 219/703 |
| 2010/0115785 A1 | 5/2010 | Ben-Shmuel et al. |
| 2010/0187224 A1 | 7/2010 | Hyde |
| 2010/0320189 A1 | 12/2010 | Buchheit |
| 2012/0067872 A1 | 3/2012 | Libman et al. |
| 2012/0103973 A1 | 5/2012 | Rogers et al. |
| 2012/0111856 A1 | 5/2012 | Nobue et al. |
| 2012/0122072 A1 | 5/2012 | Bilchinsky et al. |
| 2012/0164022 A1 | 6/2012 | Muginstein et al. |
| 2012/0312801 A1 | 12/2012 | Bilchinsky et al. |
| 2013/0080098 A1 | 3/2013 | Hadad et al. |
| 2013/0142923 A1 | 6/2013 | Tones et al. |
| 2013/0146590 A1* | 6/2013 | Einziger .................. H05B 6/64 219/709 |
| 2013/0200065 A1 | 8/2013 | Libman et al. |
| 2013/0200066 A1 | 8/2013 | Gelbart et al. |
| 2013/0284725 A1 | 10/2013 | Bilchinsky et al. |
| 2013/0306627 A1 | 11/2013 | Libman et al. |
| 2014/0287100 A1 | 9/2014 | Libman |
| 2014/0345152 A1 | 11/2014 | Ben-Shmuel et al. |
| 2015/0034632 A1 | 2/2015 | Brill et al. |
| 2015/0070029 A1 | 3/2015 | Libman et al. |

FOREIGN PATENT DOCUMENTS

| | | |
|---|---|---|
| DE | 102008029218 A1 | 12/2009 |
| EP | 0 224 423 | 6/1987 |
| EP | 1 041 860 | 10/2000 |
| EP | 1 239 372 | 9/2002 |
| EP | 1321564 A1 | 6/2003 |
| EP | 1321565 A1 | 6/2003 |
| EP | 1196649 B1 | 3/2004 |
| EP | 1742513 A2 | 1/2007 |
| EP | 2326141 B1 | 12/2012 |
| EP | 2 544 508 | 1/2013 |
| GB | 1262040 A | 2/1972 |
| GB | 2071887 A | 9/1981 |
| JP | 52-134461 | 11/1977 |
| JP | 54-134479 | 10/1979 |
| JP | 55-33783 | 3/1980 |
| JP | 55-44199 U | 3/1980 |
| JP | 56-88294 | 7/1981 |
| JP | 57-3391 | 1/1982 |
| JP | 05-312329 | 11/1993 |
| JP | 2000-357583 | 12/2000 |
| JP | 2002-532239 | 10/2002 |
| JP | 2002-349865 | 12/2002 |
| JP | 2006-86004 | 3/2006 |
| JP | 2010-080185 | 4/2010 |
| JP | 2010-092751 | 4/2010 |
| JP | 2005-242877 | 9/2017 |
| KR | 1020050058824 | 6/2005 |
| KR | 1020050058835 | 6/2005 |
| WO | 95/27388 | 10/1985 |
| WO | 97/11357 | 3/1997 |
| WO | 98/30941 | 7/1998 |
| WO | 00/36880 | 6/2000 |
| WO | 01/06050 A1 | 1/2001 |
| WO | 02/23953 | 3/2002 |
| WO | 02/35886 | 5/2002 |
| WO | 2004/010740 | 1/2004 |
| WO | 2007/096877 A2 | 8/2007 |
| WO | 2008/007368 | 1/2008 |
| WO | 2008/102360 | 8/2008 |
| WO | 2009/020959 A1 | 2/2009 |
| WO | 2009/020959 A1 | 2/2009 |
| WO | 2012/001523 A2 | 1/2012 |

OTHER PUBLICATIONS

International Search Report and Written Opinion of the International Searching Authority for PCT/US2012/053044, dated Feb. 26, 2013.
Thermo Fisher Scientific Inc., Thermo Scientific ϵ Scan In-Line Process Analyzer, product brochure, six pages, 2010.
Thermo Fisher Scientific Inc., Thermo Scientific ϵ Scan In-Line Process Analyzer, Product Specifications, two pages, 2010.
EPO Communication in EP Application No. 12773420.0 dated Nov. 17, 2016.
Paper entitled Variable Frequency Microwave Heating of Food by J. R. Bows dated 1999.
Opposition dated Mar. 17, 2016 in EP 2 544 508 and Opposition Annex.
Two Opposition Notices dated Jun. 17, 2015.
Paper entitled Frequency Agile Sources for Microwave Ovens by A. Mackay et al. dated 1979.

\* cited by examiner

OBJECT PROCESSING STATE SENSING USING RF RADIATION

This application claims the benefit of priority to U.S. Provisional Patent Application No. 61/529,361, filed on Aug. 31, 2011, and also claims the benefit of priority to U.S. Provisional Patent Application No. 61/612,961, filed on Mar. 19, 2012, both of which are incorporated herein in their entirety.

TECHNICAL FIELD

This is application relates to a device and method for applying electromagnetic energy. More particularly, but not exclusively, disclosed embodiments may relate to a device and method for applying electromagnetic energy in the radio frequency range to determine or detect a processing state of an object being processed.

BACKGROUND

Electromagnetic (EM) waves have been used in various applications to supply energy to objects. In the case of radio frequency (RF) radiation for example, RF energy may be supplied using a magnetron, which is typically tuned to a single frequency for supplying RF energy only in that frequency. One example of a commonly used device for supplying RF energy is a microwave oven. Typical microwave ovens supply RF energy at or about a single frequency of 2.45 GHz. Other apparatus have been used to process objects. For example, conventional ovens may be used to cook, heat, and dry objects. Other processing apparatus may be employed in fields of chemical production, products manufacturing, materials fabrication, etc. In each of these fields or apparatus, a need may exist to monitor the progress of a process or processes.

SUMMARY OF A FEW EXEMPLARY ASPECTS OF THE DISCLOSURE

Some exemplary aspects of the invention may be directed to methods and apparatuses for applying RF energy to detect and sense one or more processing states of an object placed in an energy application zone to be processed (e.g., to be heated). The object may be processed by applying various types of energy, for example convection heating, infrared (IR) radiating (heating), etc. In addition to applying convection and/or IR heating, RF energy may also be applied to process the object simultaneously with or instead of the IR and/or convection heating. Optionally, the RF energy may be applied before and/or after the IR and/or convection heating. Changes that may occur in the object during processing may be referred to as a processing state of the object. Some examples of processing states of an object may include: a physical property of the object (e.g., temperature, pressure, flow rate, phase(s) etc.), chemical property of the object (e.g., pH, chemical composition, etc) and if the object is a food item—the processing state of an object may include: cooking and/or doneness state of the object (e.g., thawed, proofed, fully baked/cooked etc.). Changes in the object during processing may affect the dielectric behavior and response of the object to RF energy application. One or more RF feedbacks received from the energy application zone, optionally in response to an RF energy application, may be correlated to one or more processing states of the object. The RF feedback may be monitored during the processing of the object in order to detect the one or more processing states of the object.

In some embodiments, an apparatus for applying RF energy to detect one or more processing states of an object may be provided as an add-on device which may be installed in a processing apparatus (e.g., it may be installed in cooking oven, for example: conventional MW oven, a cooking oven operated by convection, or any other device for applying heat to an object, and may indicate a cooking state of objects). It may be installed on the manufacturing site of the processing apparatus or may be installed at a later stage (e.g., after purchasing). In some embodiments an add-on device for detecting one or more processing states of an object may be provided with one or more radiating elements. Alternatively or additionally, the device may be connected to one or more radiating elements or sensors installed in the processing apparatus and may use the elements or sensors for receiving RF feedback.

Some additional embodiments may include an apparatus and method for applying RF energy to detect a cooking state of a food item placed in an energy application zone, during cooking of the food item. RF energy may be applied to the food item during cooking. Cooking the food item may be performed in a cooking apparatuses, such as: a cooking oven, a stove, an oven using an IR lamp for heating, a frying pan, an RF oven (e.g., a microwave oven) or an apparatus comprising two or more of the cooking apparatuses thereof. RF feedback may be received (e.g., by a controller) from the energy application zone. The RF feedback may by correlated with one or more processing states of the food item, for example, the temperature (e.g., is the item frozen or thawed, baked), degree of doneness, water constant, cooking state (proofed, cooked, baked, etc.). The RF feedback may be monitored during the cooking process to detect the processing state of the food item, optionally based on the correlation. In some embodiments, a computed RF feedback (to be discussed below) may be monitored during the cooking process to detect the processing state of the food item, optionally based on a correlation between the computed RF feedback and the processing state of the food item. In some embodiments, the controller may compute the computed RF feedback from the received RF feedback.

Some exemplary embodiments may include an apparatus and method for applying RF energy to detect a processing state of an object placed in an energy application zone, during processing of the object. RF energy may be applied at a plurality of excitation setups (e.g., frequencies, phases, amplitudes—as discussed below) to the object during processing. RF feedback or a computed RF feedback correlated with one or more processing states of the object may be received. The RF feedback or the computed RF feedback may be monitored during the processing of the object to detect the processing state of the object, optionally based on the correlation.

In some embodiments, the RF feedback may include a computed RF feedback. The computed RF feedback may be computed using mathematical manipulation of a raw RF feedback received from the energy application zone. A method and apparatus for applying RF energy to detect a processing state of an object placed in an energy application zone may include applying RF energy to the object during processing. In response to the RF energy application, raw RF feedback may be received (e.g., by a controller), optionally from a detector configured to receive RF signals. A computed RF feedback may be computed based on at least two values associated with raw RF feedback parameters (e.g., S-parameters, DR values at one or more frequencies, etc.).

The computed RF feedback may be correlated with one or more processing states of the object. The computed RF feedback may be monitored during the processing to detect the one or more processing states of the object.

Some exemplary embodiments of the invention disclosing a method and apparatus for determining a correlation between a processing state of an object and RF feedback. Determining the correlation may be done during processing of the object. An indication of one or more processing states of the object may be received during processing of the object. The indication may be received from at least one sensor and/or inspected by a user and received from a user interface. RF energy may be applied to an energy application zone and RF feedback may be received from the energy application zone (in response to the RF energy application) during the processing of the object. A correlation between the RF feedback and the one or more processing states of the object may be determined (by a controller).

Some other exemplary methods and apparatus may include applying RF energy to detect a processing state of an object placed in an energy application zone, during processing of the object. RF energy may be applied to the object during processing, optionally using an RF energy application unit comprising at least one radiating element, configured to apply energy to the object in order to generate RF feedback. A computed RF feedback, correlated with one or more processing states of the object may be received, by at least one controller. The controller may further be configured to monitor the computed RF feedback during the processing to detect the one or more processing states of the object. Optionally the computed RF feedback may comprise one or more results of mathematical manipulation on two or more directly measurable values of the RF feedback.

In some embodiments the method (executed by the controller) may further include receiving a correlation between the computed RF feedback and the processing state of the object. The correlation may be used to detect the one or more processing states of the object. The correlation between the computed RF feedback and the processing state of the object may be received from a memory associated with a controller. The controller may be further configured to cause the application of RF energy to the object during processing. Additionally or alternatively the correlation between the computed RF feedback and the processing state of the object may be received from a machine readable element associated with the object and may further be used to determine the one or more processing states of the object.

In some embodiments processing the object may include applying heat to the object, from a heat source. The controller may cause and/or control the heat application. Applying heat may include heating the object using convection heating source. Alternatively or additionally heat may be applied via IR heating. In some embodiments RF energy may be applied from an RF source to also to heat the object, optionally in addition to other heating source(s) (e.g., IR, convection, et.). The controller may be configured to cause application of RF energy at a plurality of excitation setups. The controller may control the application of the RF energy to heat the object at a first power level and control the application of the RF energy to receive the computed RF feedback is at a second power level, such that the first power level is higher than the second power level. Optionally RF energy is applied to heat the object at a first average amount of energy per excitation setup and to receive the computed RF feedback at a second average amount of energy per excitation setup, such that the first average amount of energy per excitation setup is higher than the second average amount of energy per excitation setup.

In some embodiments the processing state of the object may be associated with a phase of the object and/or associated with a phase of the object and/or a physical property of the object and/or a chemical property of the object. In cases where the object is a food item the one or more processing states include cooking states, for example, degree of doneness.

In some embodiments the controller may further control the processing of the object based on the one or more detected processing states of the object. The controller may further terminate the processing of the object when the one or more processing states reach a target value.

In some embodiments the computed RF feedback may be received from at least one detector configured to detect the computed RF feedback. Additionally or alternatively the at least one detector may be configured to detect RF feedback, and the computed RF feedback may be calculated based on one or more values of the RF feedback by the at least one controller. In some embodiments the detector may be associated with the radiating element. The computed RF feedback may include an indication of EM energy absorbability of the object. The controller may calculate the computed RF feedback from one or more values of an RF feedback. Optionally the received computed RF feedback may include mathematical manipulation of at least two of reflected energy, coupled energy, incident energy, S parameters or input impedance.

Some embodiments of the invention may include a display and wherein the at least one controller is configured to display a representation of the one or more processing states on the display. The display may comprise a visual display configured to display a visual representation of the one or more processing states. Additionally or alternatively the display may comprise an audio component configured to provide an audio representation of the one or more processing states.

In some embodiments the apparatus may further comprise an interface configured to receive information. The information received may include an indication of the processing state of the object. Additionally or alternatively the information may include at least one energy application protocol. In some embodiments the information may be recorded on a machine readable element and the interface may be configured to read the information from the machine readable element.

Some other aspects of the invention may be related to a machine readable element, comprising a data storage portion including one or more stored values of computed RF feedback each indicative of a processing state of the object. Optionally the one or more stored values may include values indicative of EM energy absorbability indicator of the object.

Some exemplary embodiments of the invention may include a method for processing an object placed in an energy application zone. The method may comprise applying RF energy to receive computed RF feedback; monitoring the computed RF feedback during the processing, wherein the computed RF feedback is correlated with one or more processing states of the object; and terminating the processing of the object when the computed RF feedback reaches a target value. Processing the object may include applying heat (e.g., via convection heating or IR heating) to heat the object.

Some aspects of the invention may be related to a machine readable element including data indicative of instructions for at least one controller to control processing, in an energy application zone, of an object associated with the machine readable element, the instructions may be configured to cause the at least one controller to: apply energy to the energy application zone according to a first protocol and during a first time period before RF feedback received from the energy application zone meets a criterion; and apply energy to the energy application zone according to a second protocol and during a second time period after RF feedback received from the energy application zone meets the criterion.

In some embodiments applying energy may include applying RF energy via at least one radiating element. Additionally or alternatively applying energy may include applying IR energy and/or applying convection heating.

In some embodiments the RF feedback received from the energy application zone may provide an indication of EM energy absorbability of the object.

In some embodiments the data indicative of instructions may include the criterion; optionally the criterion may include a threshold value for the RF feedback. Additionally or alternatively the data indicative of instructions may include at least one of the first protocol and the second protocol. In some embodiments data may include an identity of the object and optionally the instructions may further be configured to cause the at least one controller to select the first protocol according to the identity of the object. Alternatively the instructions may be configured to cause the at least one controller to select the first protocol according to the received RF feedback.

In some embodiments the instructions may further be configured to cause the at least one controller to select the first protocol according to an initial processing state of the object. Optionally the instructions may be configured to cause the at least one controller to determine the initial processing state of the object based on RF feedback received from the energy application zone.

In some embodiments the second protocol includes terminating the EM energy application. Optionally the at least one of the first and second protocols may include selecting one or more excitation setups from a plurality of excitation setups, and applying RF energy at the selected one or more excitation setups and/or parameters for applying RF energy. In some embodiments the at least one of the first and second protocols is a default protocol and wherein the data indicative of instructions may comprise an instruction to use the default protocol.

In some embodiments the RF feedback is correlated to a processing state of the object that changes during EM energy application. Optionally the processing state of the object that changes during EM energy application is indicated by one or more of: temperature, moisture, humidity, pressure, chemical composition, volume, weight, color, doneness level, density, taste or crispiness.

Some additional aspects of the invention may involve a method and an apparatus for controlling energy application for processing an object in an energy application zone. A controller may cause energy application to the energy application zone according to a first protocol during a first time period before an RF feedback received from the energy application zone may meet a criterion and then cause energy application according to a second protocol during a second time period after an RF feedback received from the energy application zone in the presence of the object meets the criterion. Optionally the criterion may include a threshold value for the RF feedback.

In some embodiments data indicative of instructions for processing the object may be read, from a machine readable element associated with the object, and the controller may further control the energy application according to the instructions. In some embodiments the instructions may include at least one of the first protocol and the second protocol. The at least one of the first and second protocols may include selecting at least one excitation setup from a plurality of excitation setups, and applying RF energy at the selected at least one excitation setup. Additionally or alternatively the at least one of the first and second protocols may include parameters for applying RF energy at a plurality of excitation setups. In some embodiments the at least one of the first and second protocol may be a default protocol and wherein the data indicative of instructions may comprise an instruction to use the default protocol.

In some embodiments the criterion may be read from the machine readable element.

Some embodiments may further include associating the data read from the machine readable elements with information stored in a memory. Optionally the memory may be accessible via a communication network.

In some embodiments the RF feedback comprises a value indicative of EM energy absorbable by the object.

In some embodiments energy application may include applying RF energy. Additionally or alternatively applying energy may include at least one of: applying IR energy or applying convection heating.

In some embodiments an initial processing state of the object may be determined based on RF feedback received from the energy application zone. Additionally the first protocol may be selected based on the determined initial processing state of the object. Alternatively the initial processing state of the object may be determined based on data read from the machine readable element.

In some embodiments the second protocol may include terminating the energy application.

Some embodiments may include identifying the object. Optionally the first protocol may be selected according to the identity of the object.

In some embodiments a processing state of the object, which changes during EM energy application, may be correlated to the RF feedback. The processing state of the object that changes during EM energy application may be indicated by one or more of: temperature, moisture, humidity, pressure, chemical composition, volume, weight, color, doneness level, density, taste or crispiness.

Some other embodiments of the invention may be related to a machine readable element to be associated with an object to be processed in an energy application zone, wherein the machine readable element may comprise data indicative of a criterion for changing RF energy application, via at least one radiating element, from a first protocol to a second protocol. Optionally criterion may be met when a value associated with RF feedback received from the energy application zone exceeds a threshold.

The drawings and detailed description which follow contain numerous alternative examples consistent with the invention. A summary of every feature disclosed is beyond the object of this summary section. For a more detailed description of exemplary aspects of the invention, reference should be made to the drawings, detailed description, and claims, which are incorporated into this summary by reference.

DETAILED DESCRIPTION

Figure 1A:
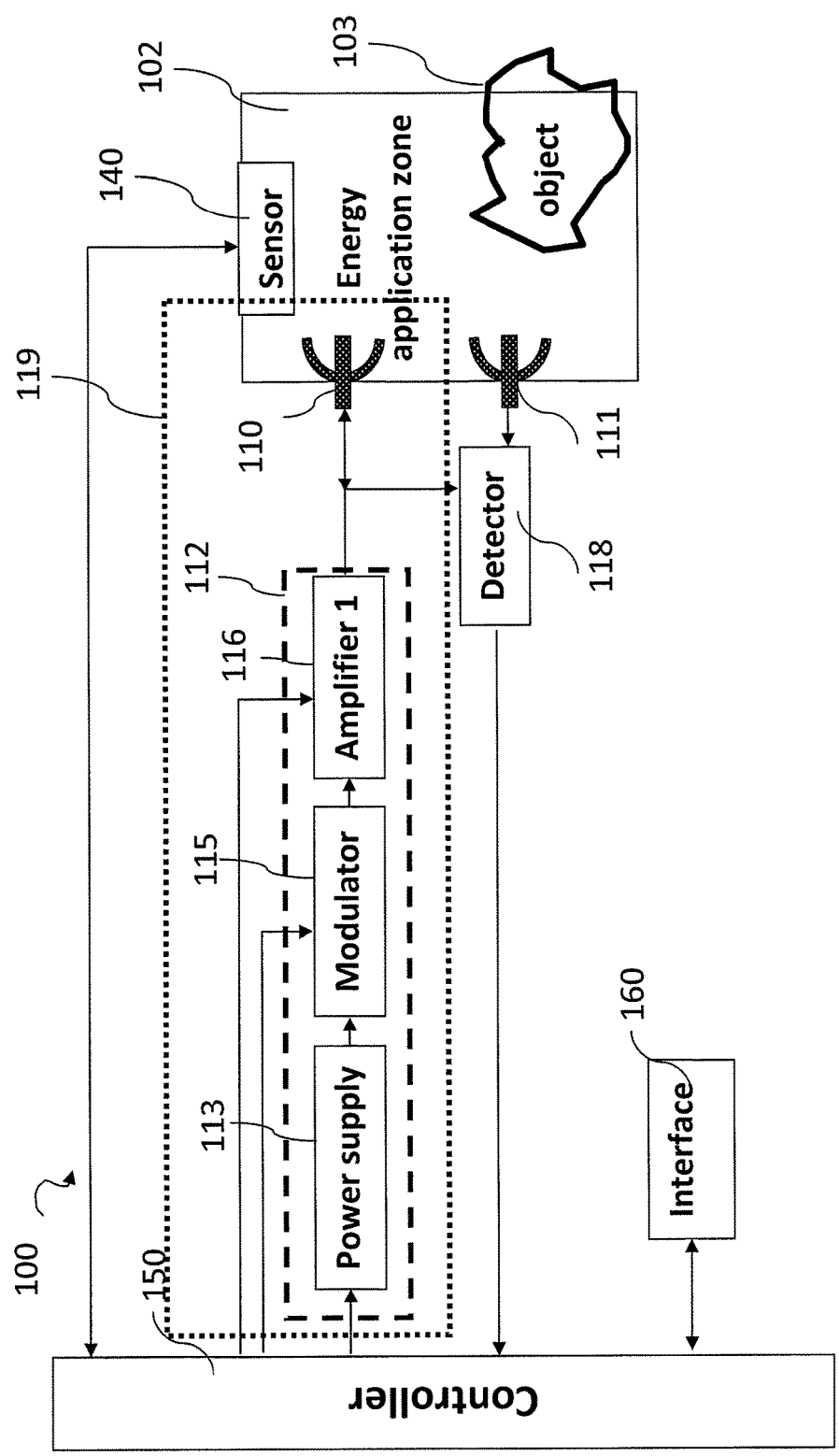
FIGS. 1A and 1B include diagrammatic representations of exemplary apparatuses for applying RF energy to an object, in accordance with some exemplary embodiments of the present invention.

Reference will now be made in detail to exemplary embodiments of the invention, examples of which are illustrated in the accompanying drawings. When appropriate, the same reference numbers are used throughout the drawings to refer to the same or like parts.

In one respect, the disclosed embodiments may involve apparatuses and methods for applying EM energy. The term EM energy, as used herein, includes energy deliverable by EM radiation in all or portions of the EM spectrum, including but not limited to, radio frequency (RF), infrared (IR), near infrared, visible light, ultraviolet, etc. In one particular example, applied EM energy may include RF energy with a wavelength in free space of 100 km to 1 mm, which corresponds to a frequency of 3 KHz to 300 GHz, respectively. In some other examples, the applied EM energy may fall within frequency bands between 500 MHz to 1500 MHz or between 700 MHz to 1200 MHz or between 800 MHz to 1 GHz. Applying energy in the RF portion of the EM spectrum is referred herein as applying RF energy. Microwave and ultra high frequency (UHF) energy, for example, are both within the RF range. In some other examples, the applied EM energy may fall only within one or more industrial, scientific and medical (ISM) frequency bands, for example, between 433.05 and 434.79 MHz, between 902 and 928 MHz, between 2400 and 2500 MHz, and/or between 5725 and 5875 MHz. Even though examples herein are described in connection with the application of RF energy, these descriptions are provided to illustrate a few exemplary principles of the invention, and are not intended to limit the invention to any particular portion of the EM spectrum.

Some embodiments of the invention may be related to apparatuses and methods for processing object(s), optionally by applying heat to the object, from a heat source. Heat may be applied to thaw a frozen object, to cook or bake a food item, to accelerate a chemical reaction, to dry objects (e.g., clothes), to sinter parts (e.g., powder parts), to cure polymers, etc. The heat may be applied by a convection heat source, including, for example, a heating element, such as a filament. Additionally or alternatively, the heat may be applied from an IR source, for example, an IR lamp. Optionally, the heat may be applied from an RF source configured to supply RF energy, for example a magnetron or a solid-state power amplifier. In some embodiments, two or more types of heat sources may be used to process the object. Two or more types of heat sources may be applied simultaneously or sequentially, or both. For example, RF energy and convection heating may be applied simultaneously for part or all of the time energy is applied to process the object. In some embodiments, the different energy sources may be applied alternately or consecutively. The application is not limited to any particular heat source or sources.

In some embodiments, RF energy may be applied to sense (i.e., detect, monitor, etc.) one or more processing states of an object before, during and/or after processing of the object. In some embodiments, the processing state may be sensed (detected) by monitoring RF feedback. The RF feedback may be received in response to the RF energy application. RF energy application apparatuses for sensing one or more processing states of an object are diagrammatically presented in FIGS. 1A and 1B. In some embodiments, RF energy may be applied to object 103 before the processing, to detect and determine the initial state of object 103. RF energy may be applied to object 103 during processing, for example, in order to monitor changes in the object that occur due to the processing (e.g., heating) of the object. Some examples of such changes may include a phase change (e.g., thawing of a frozen object), pH change due to a progress of a reaction in a reactant solution, polymerizing of polymers due to curing, denaturation of proteins (e.g., in cooking of egg-based dishes and pastries and cooking of meat), various cooking states (e.g., baking of dough), etc. Those changes may be associated with one or more processing states of the object. The RF energy may also be applied near or at the end of the processing, for example, in order to determine if the process should be terminated.

In some embodiments, RF energy may be applied (e.g., in apparatus 100) to correlate between a processing state of object 103 (e.g., indicated by at least one processing state indicator) with RF feedback received from an energy application zone during processing of the object. A processing state indicator may include any mechanism that is configured to convey to the controller information regarding the processing state of the object. For example, the processing state indicator may comprise or be one or more sensors configured to sense one or more conditions, attributes, etc. indicative of the processing state of the object, e.g., a temperature sensor, a humidity sensor etc. Additionally or alternatively, the processing state indicator may comprise or be a user interface configured to receive from a user an indication of the processing state of the object and convey this indication to the controller.

The indication of the processing state may be sensed by one or more sensors provided in the energy application zone or may be provided by a user through an interface. An indication of a processing state may include any measurements of a physical or chemical properties of the object either quantitatively (e.g., temperature, pressure etc.) or non-quantitatively (e.g., color, degree of doneness, taste, cooking state, etc.) of an object before, during or after processing of the object. The indication of the processing state may be measured (sensed) by a sensor (e.g., sensor 140) or may be determined through inspection by a user. Apparatus 100 may further include a first user interface (e.g., interface 160) configured to receive from a user an indication of the processing state of the object. Some examples of quantitatively variable indicative of the processing state of the object may include: temperature, humidity, pressure, flow rate, pH, chemical composition, density, weight, volume, etc. Some examples of non-quantitatively measurable variable indicative of the processing state may include: color, taste, cooking state, doneness level etc. As used herein, cooking state may refer to any possible state of an object, either desired or undesired, that may occur relative to a food item during any form of cooking/processing (e.g., roasting, baking, boiling, steaming, grilling, slow cooking, thawing, browning, dough proofing etc.) of the food item. Some examples for cooking states may include: the end of baking of dough, the beginning and end of softening stage in slow cooking of meat or cooking of starchy vegetables, end of proofing of yeast dough, end of browning of various baking products, degree of doneness of various meats, or degree of any other type of cooking process, etc.

Sensing (i.e., detecting, monitoring, etc) one or more processing states of an object may be performed by applying RF energy to an energy application zone, e.g., zone 102 in order to receive RF feedback from the object. The RF feedback may be correlated with the one or more processing states of the object. Method 330 for correlating RF feedback and one or more processing states of the object is described in reference to FIG. 3C. The correlation may be recorded, for example, on a memory associated with apparatus 100 (e.g., a memory associated with controller 150) or on a machine readable element (e.g., a barcode).

As used herein, RF feedback may include any received RF signal or any value calculated based on one or more received RF signals, which may be indicative of the dielectric response of the cavity and/or the object to EM fields excited in the cavity. RF feedback may be excitation setup-dependent and may include, for example, values that vary over different excitation setups. RF feedback may include raw RF feedback and computed RF feedback. The raw RF feedback may include directly measurable parameters, for example, input and output power levels, field intensities, network parameters, e.g., scattering (S) parameters of the cavity, admittance (Y) parameters, reflection and transmission coefficients, impedances, etc. The computed RF feedback may include a result of any mathematical manipulation on two or more directly measurable parameters or values, for example, sums, multiplicative products, ratios, and/or differences between directly measurable parameters, dissipation ratio values (DR) (as discussed below), averages (e.g., time-average and/or excitation setup-average), of directly measurable parameters or of computed parameters; derivatives (e.g., time derivatives and/or excitation setup derivatives) of directly measurable parameters or of computed parameters, etc. The concept of excitation setups is broadly discussed below.

In some embodiments, RF feedback may be responsive to RF energy (i.e., EM energy in the RF range) application. RF energy may be applied to an energy application zone at least partially occupied by an object. The RF energy applied to receive the RF feedback may be at relatively low energy amounts, e.g., at a low power level. As used herein, low energy amounts may refer to amounts of energy that result in little or no processing of an object or that are otherwise too low to provide a desired degree of a processing. For example, in some embodiments, a low energy amount may be insufficient to cause a change (or a change of a certain degree) in at least one detectable processing state of the object. In some embodiments, applying RF energy to process (e.g., heat) the object may be at a first average amount of energy per excitation setup and applying RF energy to receive the RF feedback may be at a second average amount of energy per excitation setup, and the first average amount of energy per excitation set is higher than the second average amount of energy per excitation setup.

The RF feedback may include signal(s) received in response to the RF energy application by detectors (e.g., detectors 118, 118a, 128, 138) or sensors (e.g., sensor 140) placed in or around the energy application zone. The signal(s) may include any or all directly measurable parameters associated with the RF energy application. Energy may be supplied to at least one radiating element (e.g., element 110 illustrated in FIGS. 1A and 1B), and energy may be reflected back from the energy application zone to the emitting radiating element in response to the application of the RF energy. Additionally or alternatively, energy may be coupled to other radiating elements (e.g., element 111 illustrated in FIG. 1A and elements 120 and 130 illustrated in FIG. 1B). Various examples of RF feedback that may be received in response to RF energy application are discussed below.

In some embodiments, the processing of the object (e.g., by applying energy to the object) may be controlled based on the received RF feedback and/or the detected processing state. For example, the amount of energy (e.g., the temperature of a conventional cooking oven or the power level in a microwave oven) or the duration of the energy application (e.g., the length of time of the energy application) may be determined based on the received RF feedback (e.g., computed RF feedback). In an exemplary embodiment, computed RF feedback may be monitored during the application of heat in a conventional oven (e.g., during baking). The computed RF feedback may be monitored during heating of the food item at a first temperature (e.g., 180° C.) until the computed RF feedback indicate(s) that the food item has been cooked to a certain degree, after which, the heat application may be terminated.

In some embodiments, a protocol in which energy is applied to process the object may be determined based of an RF feedback (e.g., computed RF feedback). As use herein, a protocol may include one or more of the parameters that controls the energy application, for example, the temperature and the duration of heating in a convection heating (for example: heating at temperature $T_1$ for $S_1$ seconds followed by heating at temperature $T_2$ for $S_2$ seconds etc.), the power and the time IR heating. When RF energy is applied to process the object—the protocol may include: setting RF energy levels (e.g., power levels and/or time durations) and/or selecting one or more excitation setups from a plurality of excitation setups, and applying RF energy at the selected excitation setups, one or more rules for energy application as a function of the RF feedback etc. Energy may be applied to process an object using a first protocol (e.g., temperature and time may be set to cook a food item). RF feedback may be monitored during the energy application until one or more RF feedback value reaches a threshold value (i.e., a first criterion) indicative of a first processing state of the object (e.g., the food item is cooked). After the RF feedback value reaches the threshold value, a second protocol may be applied by elevating the temperature (e.g., to 220° C.) for a short period of time in order to brown the food item. The processing (e.g., heating) may be terminated (i.e., a third protocol) when the monitored RF feedback indicates that the one or more states (e.g., a second state) of processing have reached a target value or a second criterion (e.g., a desired temperature, or a desired degree of doneness, or a target pH, etc.) was met. Exemplary methods 300 and 310 for controlling energy application to an object based on RF feedback are disclosed in FIGS. 3A and 3B and exemplary method 400 for controlling RF energy application based on a criterion is disclosed in FIG. 4.

In certain embodiments, RF energy may be applied (e.g., to sense at least one processing state of an object) in an energy application zone. For example, RF energy may be applied to the energy application zone, such as energy application zone 102, illustrated in FIGS. 1A and 1B. As indicated above, other energy types (e.g., convection and/or IR) may be applied to the zone in order to process the object. Energy application zone 102 may include any cavity, void, location, region, or area where energy may be applied to process the object. In some embodiments, RF energy may be applied to sense and/or detect a processing state of the object. The zone may be hollow, or may be filled or partially filled with liquids, solids, gases, or combinations thereof. By way of example only, energy application zone 102 may include an interior of an enclosure, interior of a partial enclosure, open space, solid, or partial solid that allows existence, propagation, and/or resonance of EM waves. Zone 102 may include a conveyor belt or a rotating plate. In some embodiments, zone 102 may include or be a cavity (for example: exemplary cavity 200 as illustrated in FIG. 2A).

Figure 2A:
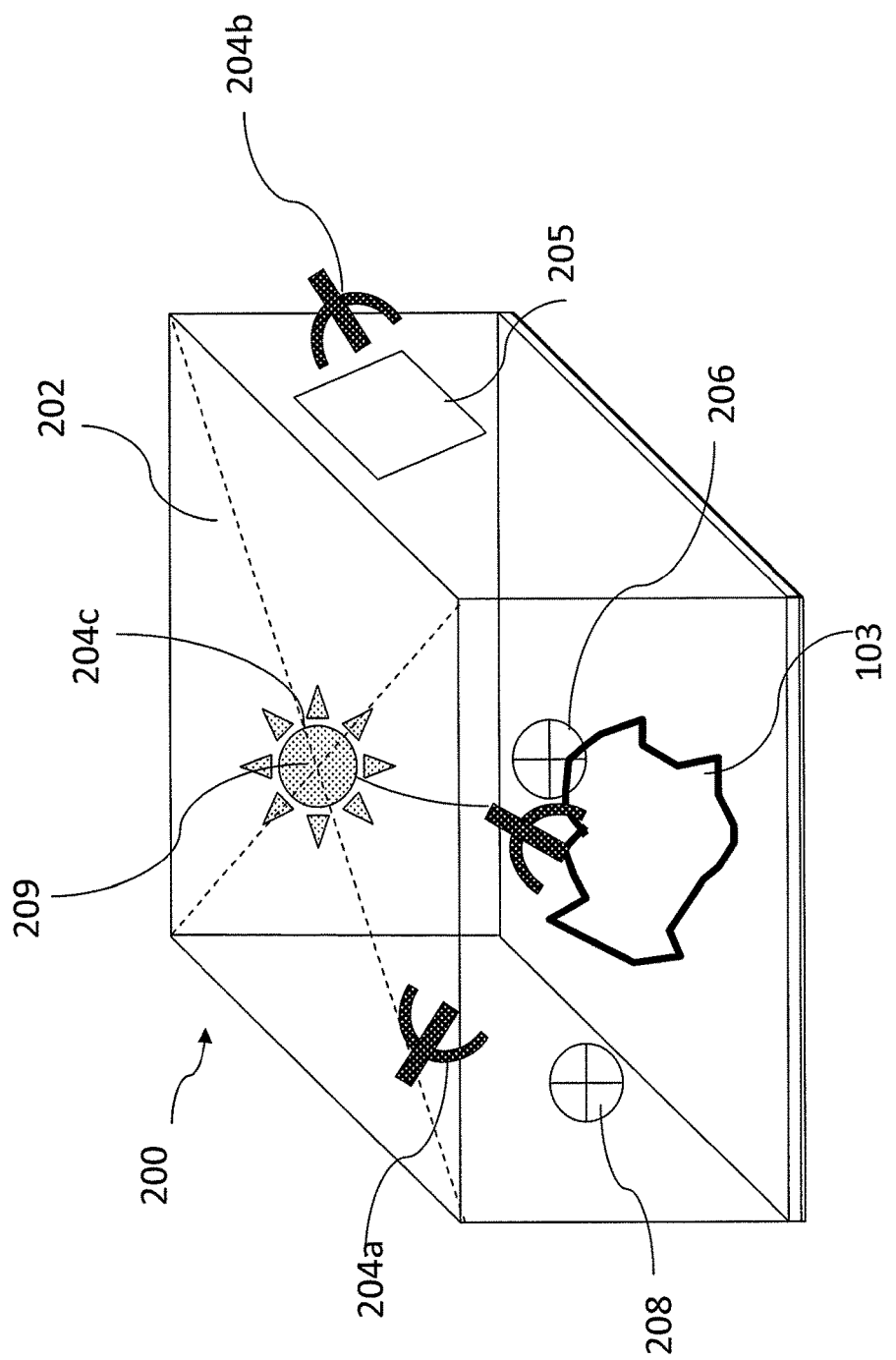
FIGS. 2A-2B include diagrammatic representations of cavities, in accordance with some exemplary embodiments of the present invention.

In certain embodiments, EM energy may be applied to sense and detect a processing state of an object, e.g., object 103 in FIG. 1A, placed in the energy application zone, e.g., energy application zone 102. An object may be considered in the energy application zone if at least a portion of the object is located in the zone or if some portion of the object receives applied EM radiation. The type of object to which EM energy may be applied for processing is not limited to a particular form of the object. An object may include a liquid, semi-liquid, solid, semi-solid, or gas, depending upon the particular process with which the disclosed embodiment is utilized. The object may also include composites or mixtures of matter in differing phases. Thus, by way of non-limiting example, the term object may encompass such matter as food to be defrosted or cooked; clothes or other wet material to be dried; frozen organs to be thawed; chemicals to be reacted; fuel or other combustible material to be combusted; hydrated material to be dehydrated, gases to be expanded; liquids to be heated, boiled or vaporized, or any other material for which there is a desire to apply, even nominally, energy (e.g, EM energy).

In some embodiments, a portion of RF energy applied to energy application zone 102 may be absorbed (dissipated) by object 103. In some embodiments, another portion of the EM energy applied to energy application zone 102 may be absorbed by various elements (e.g., food residue, particle residue, additional objects, structures associated with zone 102) or any other EM energy-absorbing materials found in zone 102 or associated with energy application zone 102. Energy application zone 102 may also include loss constituents that may not, themselves, absorb an appreciable amount of EM energy, but otherwise account for EM energy losses. Such loss constituents may include, for example, cracks, seams, joints, door(s), interface between cavity body and a door, or any other loss mechanisms associated with energy application zone 102. Thus, in some embodiments, energy dissipated in the zone may include energy dissipated in at least a portion of object 103 along with any EM energy-absorbing constituents in the energy application zone as well as any EM energy loss constituents associated with the zone.

Exemplary energy application zone 102 may include locations where energy is applied: an oven (e.g., a cooking oven), chamber, tank, dryer, thawer, dehydrator, reactor, engine, chemical or biological processing apparatus, pipe (e.g., fuel pipe), furnace, incinerator, material shaping or forming apparatus, conveyor, combustion zone, filter, cooler, freezer, etc. In some embodiments, the energy application zone may be part of a vending machine, in which objects are processed once purchased.

Figure 1B:
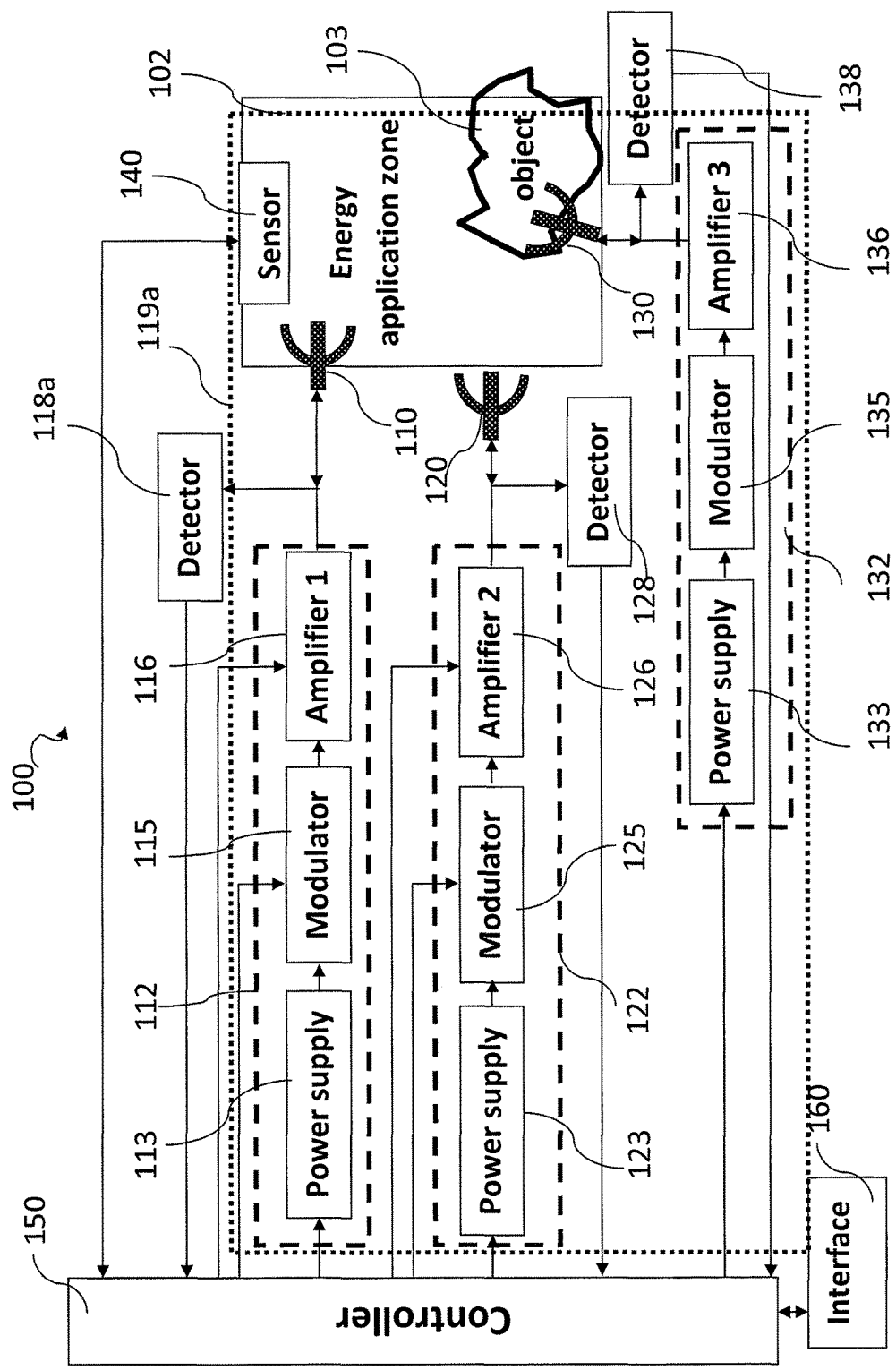

FIGS. 1A and 1B include diagrammatic representations of an apparatus 100 for applying RF energy to an object (e.g., to detect one or more processing states of the object) placed in zone 102, for example during processing of the object. RF energy may include EM energy applied at frequencies in the RF range. Apparatus 100 may include at least one radiating element 110 configured to apply RF energy to energy application zone 102. Radiating element 110 may include any element, system, array of elements, etc. designed or configured to transmit (emit) RF energy. For example, radiating element 110 may include: any antenna, an array of antennas, an RF feed, a waveguide, a slow wave antenna, a patch antenna, inverted F antenna, etc. in any combination or numbers thereof. In the presently disclosed embodiments, more than one antenna and/or a plurality of radiating elements (e.g., antennas) may be provided (e.g., radiating elements 110 and 111 illustrated in FIG. 1A or radiating elements 110, 120 and 130 illustrated in FIG. 1B). Energy application zone 102 may include an enclosure with defining surfaces. The radiating elements may be located on one or more of the surfaces that define zone 102 (e.g., cavity walls). For example, radiating elements 110 and 130 may be located on two different (e.g., opposing) surfaces of energy application zone 102. In some embodiments, one or more of the radiating elements may be located inside zone 102 (e.g., element 130) or partially located inside zone 102 (e.g., elements 110 and 111). Additionally or alternatively, a radiating element may be located outside the energy application zone (e.g., element 120). One or more of the radiating elements (e.g., element 130) may be near, in contact with, in the vicinity of or even embedded in object 103 (e.g., when the object includes a liquid, or a filter, for example—radiating element 204c illustrated in FIG. 2A). The orientation, type, dimensions and/or configuration of each radiating element may be distinct or the same, based on a specific application, e.g., based on a desired target effect. Each radiating element may be positioned, adjusted, and/or oriented to emit EM waves along a same direction, or various different directions. Furthermore, the location, orientation, and configuration of each radiating element may be predetermined before applying energy to the object. Alternatively or additionally, the location, orientation, and/or configuration of each radiating element may be dynamically adjusted, for example, by using a controller (e.g., controller 150), during operation of the apparatus and/or between rounds/cycles of energy application. Radiating elements of any structure or configuration may be used with the disclosed embodiments.

As shown in FIG. 1A, apparatus 100 may include at least one radiating element 110 for emitting RF energy to energy application zone 102 and at least one radiating element 111 may be configured to receive EM energy from energy application zone 102. A radiating element may function as an emitter, a receiver, or both, depending on a particular application or configuration. When a radiating element acts as a receiver of RF energy from an energy application zone (e.g., received reflected and/or coupled EM waves), the radiating element receives RF energy from the energy application zone or from other radiating elements. In some embodiments, radiating element 110 may function as emitter and receiver.

Some aspects of the present invention may involve detecting, measuring, monitoring or sensing: RF energy emitted from the radiating element to energy application zone 102, RF energy supplied to the emitting radiating element, or RF energy received by the radiating element(s) (e.g., elements 110 and 111) from the energy application zone, to detect one or more processing states of the object. A detector configured to measure and/or detects and/or calculate various RF feedback of the emitted and/or received (e.g., reflected or coupled) RF energy may be associated with at least one radiating element. In some embodiments, the detector may include a directional coupler associated or connected to a radiating element. The detector may detect and/or measure RF feedback (e.g., raw RF feedback) related to the RF energy emitted and/or received. The raw RF feedback may be associated with one or more processing states of the object. The raw RF feedback may include all detectable parameters of the RF emission, for example: power, frequency, energy, current, voltage, phases between emissions, etc. For example, detector 118, illustrated in FIG. 1A, may be associated with radiating element 110 and 111. Detector 118 may be configured to measure or detect one or more parameters related to element 111, for example, responsive to the RF energy emission from element 110. In some embodiments, detector 118 may be configured to detect the parameters of the RF energy received from zone 102 (e.g., reflected back) to element 110 as a result of the RF energy emission from element 110. Detector 118 may also include suitable types of circuits or devices that measure the voltage and current at the ports of radiating elements 110 and 111. In some embodiments, detector 118 may include a directional coupler, configured to allow signals to flow from the RF source (e.g., source 112) to the radiating elements when the radiating elements function as emitters, and to allow signals to flow from the radiating elements to the detector when the radiating elements function as receivers. Detector 118 may further include a controller configured to perform mathematical manipulation of the raw RF feedback to receive (obtain) a computed RF feedback. Alternatively or additionally, the computed RF feedback may be calculated by controller 150 and the detector may send the raw RF feedback to controller 150 for further manipulation.

In some embodiments, detector 118 may be associated with two elements (e.g., elements 110 and 111). In some embodiments, each element may be associated with a detector. For example, elements 110, 120 and 130 may be associated with detectors 118a, 128 and 138 illustrated in FIG. 1B. Detectors 118a, 128 and 138 may be configured to detect RF energy parameters of both the emitted and the received RF energy from zone 102. For example, RF energy may be emitted from element 110 to zone 102. As a result, a portion of the RF energy may be absorbed by or dissipated in object 103, and another portion may be reflected back or coupled from zone 102 and received by elements 110, 120 and 130.

Consistent with some disclosed embodiments, RF energy may be supplied to one or more emitting radiating elements from RF source 112. Energy supplied to the emitting radiating element (e.g., element 110) from RF source 112 may be referred to as supplied energy and denoted as SE.

Some of the supplied RF energy may be absorbed by the object (e.g., object 103). This portion of energy may be referred to as absorbed energy or dissipated energy and denoted as AE.

A portion of the supplied RF energy may be reflected back to the emitting element (e.g., element 110). This portion of energy may be referred to as reflected energy and denoted as RE. The reflected energy may be reflected at the interface between the radiating element and the energy application zone. Alternatively or additionally, the reflected energy may include energy that is reflected from the energy application zone (e.g., due to impedance mismatch), for example, from the object or from a wall defining the zone, etc.

Other portions of the supplied energy may be coupled to other radiating elements or sensors in the energy application zone (for example, receiving radiating elements—e.g., element 111, another emitting radiating element (e.g., 120 and 130), a sensor (e.g., sensor 140)) and may be referred to as coupled energy and denoted as CE.

In some embodiments, the supplied RF energy (SE) may include energy that is reflected (RE) back to the emitting radiating element, absorbed (AE) in the object, and coupled (CE) to one or more of other radiating element(s). Equation (1) may represent a relationship between quantities SE, RE, AE, and CE, as follows:

$$SE=RE+AE+CE \quad (1)$$

The difference between the amount of energy supplied to a radiating element and the amount of energy reflected back to that radiating element may be referred to as delivered energy and may be denoted as DE. One or more detectors (e.g., detector 118, 118a, 128 and 138) may be configured to detect and measure the supplied, reflected, and coupled energy values, and a controller (e.g., controller 150) may be configured to determine the delivered and/or absorbed amounts of energy, for example, based on equation (1). This may result in the following equations:

$$AE=SE-(RE+CE) \quad (2a)$$

$$DE=SE-RE \quad (2b)$$

$$DE=AE+CE \quad (2c)$$

Apparatus 100 may further include a source for supplying RF energy to the radiating element(s). For example, source 112 may supply RF energy to emitting element 110, source 122 may supply RF energy to emitting element 120, and source 132 may supply RF energy to emitting element 130.

In accordance with some embodiments of the invention, an apparatus or method may involve the use of at least one source configured to supply RF energy to the energy application zone. A source may include any component(s) that may be suitable for generating and supplying RF energy. For example, source 112 may include an RF power supply (e.g., power supply 113). In yet another example, the source may include more than one power supply (e.g., 113, 123 and 133). Each of the power supplies may be configured to generate EM waves that carry EM energy. For example, power supply 113 (or 123 or 133) may include a magnetron configured to generate high power microwaves at a predetermined wavelength or frequency. Alternatively or additionally, power supply 113 (or 123 or 133) may include a semiconductor oscillator, e.g., a voltage controlled oscillator, configured to generate AC waveforms (e.g., AC voltage or current) with a controllable frequency. The frequency may be controlled to be constant or to vary. AC waveforms may include sinusoidal waves, square waves, pulsed waves, triangular waves, or another type of waveforms with alternating polarities. Alternatively or additionally, a source of RF energy may include any other power supplies, e.g., EM field generator, EM flux generator, or any mechanism for generating vibrating electrons. The source may include a solid state amplifier.

Consistent with some embodiments, RF energy may be supplied to the energy application zone in the form of propagating RF waves at predetermined wavelengths or frequencies (also known as RF radiation). As used herein, propagating RF waves may include resonating waves, traveling waves, evanescent waves, and waves that travel through a medium in any other manner. RF radiation carries energy that may be imparted to (or dissipated into) matter with which it interacts.

In some embodiments, the source (e.g., source 112, 122 or 132) may further include at least one modulator (e.g., modulator 115, 125 or 135) and/or at least one amplifier (e.g., amplifier 116, 126 or 136). The modulator may include a phase modulator, a frequency modulator, an amplitude modulator, an oscillator or any other modulator configured to modulate at least one aspect of the RF energy supplied to the radiating element. The amplifier may include any apparatus configured to change (e.g., amplify) the amplitude of the RF waves supplied by the power supply. It is to be noted that the source (e.g., source 112, 122 or 132) may include only one component or more than one component or any combination of components according to the requirements of particular embodiment. The power supply, the modulator, and/or the amplifier may each be controlled by a controller (e.g., controller 150), as will be discussed in greater detail below.

Apparatus 100 may further include at least one sensor, such as sensor 140. Sensor 140 may be installed in or around energy application zone 102. In some embodiments, sensor 140 may constitute an exemplary processing state indicator. Sensor 140 may be configured to detect and/or measure RF feedback in accordance with some embodiments of the invention. For example, sensor 140 may be configured to monitor the intensity of EM field excited in the energy application zone. Additionally or alternatively, sensor 140 may be configured to detect and/or measure other signals or feedback indicative of one or more processing states of the object or the energy application zone. For example, sensor 140 may include a thermometer configured to measure a temperature associated with the object and/or the energy application zone (e.g., a thermocouple or an IR sensor). Sensor 140 may include a humidity sensor, a pressure sensor (e.g., a barometer), a pH sensor configured to measure the pH value of a solution (e.g., when the object comprises liquids), a flow meter, etc. Sensor 140 may be configured to measure the weight of at least a portion of the object (e.g., a scale). Sensor 140 may be configured to measure any detectable and measurable property (e.g., an indicator for the processing state) of the object or the energy application zone. Sensor 140 may be configured to send feedback signals to controller 150. In some embodiments, two or more sensor 140 may be provided. The two or more sensors 140 may include one or more different types or the same types of sensors (e.g., a temperature sensor, fiber optics for detecting temperature, a weight sensor, etc. may be provided). Some aspects of the invention may involve correlating, e.g., by controller 150, the signal(s) detected at sensor 140 that are indicative of the processing state of object 103, with RF feedback sensed, monitored or detected by detectors 118, 118a, 128 and/or 138, in parallel or in addition to the signal(s) received from sensor 140.

In some embodiments, apparatus 100 may include a controller (e.g., controller 150). Controller 150 may be coincident with or may be part of processor. As used herein, the term "processor" may include an electric circuit that performs a logic operation on input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations.

The instructions executed by the controller (e.g., one or more scripts or energy protocols) may, for example, be pre-loaded into a memory unit integrated with or embedded into the controller or may be stored in a separate memory unit, such as a RAM, a ROM, a hard disk, an optical disk, a magnetic medium, a flash memory, other permanent, fixed, or volatile memory, or any other mechanism capable of storing instructions for the controller. The separate memory unit may or may not be a part of the controller. The controller may be customized for a particular use, or can be configured for general-purpose use and can perform different functions by executing different software.

If more than one controller or processor is employed, all may be of similar construction, or they may be of differing constructions electrically connected or disconnected from each other. They may be separate circuits or integrated in a single circuit. When more than one controller or processor is used, they may be configured to operate independently or collaboratively. They may be coupled electrically, magnetically, optically, acoustically, mechanically or by other means permitting them to interact.

An apparatus according to some embodiments of the invention may include one or more RF energy application units, for example units 119, and 119a, illustrated in FIGS. 1A and 1B. An energy application unit (e.g., unit 119a) may include one or more radiating elements, e.g., elements 110, 120 and 130, and an RF energy source supplying RF energy to the radiating element(s). In some embodiments, RF energy application unit 119a may include two or more synchronized RF energy sources, e.g., sources 112, 122 and 132, which may be controlled by, for example—by controller 150, to supply to the radiating elements signals having a common frequency, at a controlled phase difference, at a controlled amplitude difference, etc. In some embodiments, unit 119a may include two or more non-synchronized RF energy sources. In some embodiments, the effect of applying energy from one or more of the RF energy application units in series or during non-overlapping or partially overlapping time periods may result in substantially the same as the effect as applying energy from one or more or all of the RF energy application units simultaneously. Embodiments consistent with the present invention may include one or more energy application units.

An RF energy application unit according to some embodiments may apply energy at two or more different excitation setups. Applying energy at different excitation setups may result in excitation of different field patterns in energy application zone 102. The excitation setups (ES) may differ from one another by one or more values of parameters that may affect the field pattern and may be controlled by controller 150. Such a parameter is referred to herein as a controllable field affecting parameter (c-FAP). In some embodiments, a value may be selected for each c-FAP, and the excitation setup may be defined by the selected values. Varying a selected value of even one c-FAP may vary the excitation setup, which, in turn, may vary the field pattern excited in the energy application zone.

In some cases, varying values of c-FAPs may result in significant variations in the generated field patterns. In other instances, however, varying values of c-FAPs may produce little or no change in the generated field patterns (e.g., if the variation between the two values of the c-FAP is small).

To obtain a mental image of an excitation setup and how it may be set, one may imagine an RF energy application unit according to some embodiments of the invention to be controlled from a switchboard. The switchboard may include a set of knobs, dials, switches, or other value-selectors, each for determining the value of (or selecting a value for) one c-FAP. Switching from one excitation setup to another may be accomplished by manipulating one (or more) of the value-selectors to select a different value. The position of all the value selectors collectively (e.g., the positions of all the knobs, dials and switches collectively) may define a single excitation setup. While this mental image may be helpful, in practice, an RF energy application unit may be controlled by a controller, which may set the values of the available c-FAPs by using micro-switches, transistors, electronic circuitries, and other value selectors, which may look differently than knobs and dials.

Applying energy at a particular excitation setup may excite an EM field in energy application zone 102. For brevity, this EM field may be referred to as an excitation. Thus, each excitation setup may correspond to an excitation, and a reference to supply, reception, absorption, leaking, etc. of an excitation setup may refer to supply, reception, absorption, leaking, etc. of the corresponding excitation. Thus, for example, a statement that a given excitation or excitation setup is absorbed in the object may mean that an EM field excited by the energy application unit (e.g., unit 119) at the given excitation setup results in energy absorbed in the object.

Different apparatuses may be able to control different field affecting parameters. For example, in some embodiments, controller 150 may control the frequency of an EM wave applied by energy application unit 119 to energy application zone 102. In such embodiments, the frequency may be available as a controllable field affecting parameter (c-FAP). In one example, controller 150 may control the frequency to have any of two or more values, e.g. 800 MHz, 800.5 MHz, etc. By controlling the frequency and changing from one frequency value to another, the excitation setup may be changed, which, in turn, may change the field pattern excited in the energy application zone.

In another example, an energy application unit (e.g., unit 119*a*) may include two radiating elements (e.g., elements 110, 120 and 130) that emit radiation at a controllable phase difference. The phase difference may be controlled, by controller 150, to have two or more values, e.g., 0°, 90°, 180°, or 270°. The phase difference between EM fields emitted by the two radiating elements may be available to the apparatus comprising the energy application unit as a c-FAP.

In another example, a difference between intensities at which two radiating elements emit EM fields of the same frequency may be controlled, and thus may be available as a c-FAP.

In another example, an energy application zone (e.g., zone 102) may include one or more conductive elements (e.g., rods), each of which may be controlled, e.g., by controller 150, to be either in a parasitic state or in a connected state. The value of the state of each rod (i.e. parasitic or connected) may affect the EM field pattern excited in the energy application zone. In apparatuses having such rods, the state of each rod may constitute a c-FAP.

In another example, an energy application zone may include a magnetizable element (e.g., at a wall of the energy application zone) and an electromagnet near the magnetizable element. The magnetizable element and the electromagnet may be arranged such that a field pattern excited in the energy application zone may be affected by current flowing in the electromagnet. In some embodiments, controller 150 may be configured to control the value of the current in the electromagnet (e.g., 1 mA, 20 mA, 500 mA, etc.). The value of the current may be available as a c-FAP.

In another example, energy application unit 119*a*, illustrated in FIG. 1B may include a plurality of radiating elements 110, 120 and 130, and each may be turned on or off. In such embodiments, the status of each radiating element (i.e., on or off) may be available as a c-FAP. Additionally, or alternatively, the total number of radiating elements turned on may constitute a c-FAP.

Other examples of parameters that may serve as controllable field affecting parameters in some embodiments may include the position of a radiating element, orientation of a radiating element, cavity dimensions, or any other controllable parameter, the value of which may affect the field pattern excited in the energy application zone upon RF energy application to the zone.

Excitation setups (ES) of apparatuses configured to control only a single c-FAP may be referred to as one-dimensional excitation setups. An excitation setup of an apparatus that controls multiple c-FAPs may be referred to as multi-dimensional excitation setup. In general, the number of c-FAPs available to an apparatus determines a dimension of the excitation setups available to the apparatus. The collection of all the excitations that may be excited by an apparatus (or the collection of all the excitation setups available to an apparatus) may be referred to as the excitation space of the apparatus. The dimension of an excitation space of an apparatus may be the same as the dimension of each excitation setup available to that apparatus.

In some embodiments, an RF energy application unit may be controlled by a controller (e.g., controller 150), configured to control RF energy application based on an RF feedback.

Thus, in some embodiments, when RF energy is applied to heat the object as well as to sense a processing state of the object, RF energy application may be controlled such that one or more aspects of energy application at a given excitation setup (e.g., amount of energy, power level at which energy is applied, time duration at which energy is applied etc.) may depend on RF feedback received to the same excitation, to a different excitations, or over multiple excitations. At these embodiments, RF energy may be applied in an amount sufficient to process the object, i.e., in an amount sufficient to cause a change in at least one property (e.g., a processing state) of at least a portion of the object (e.g., to raise the temperature of at least a portion of the object). In some embodiments, applying RF energy to process (e.g., heat) the object may proceed at a first power level (e.g., a script) and applying RF energy for purposes of generating (receiving) RF feedback may proceed at a second power level. In some embodiments, the first power level is higher than the second power level. In some embodiments, RF energy applied to heat the object may be at a first average amount of energy per excitation setup and RF energy applied to receive the RF feedback may be at a second average amount of energy per excitation setup, and the first average amount of energy per excitation set is higher than the second average amount of energy per excitation setup.

The controller may be configured to select a subgroup of excitation setups (or at least one excitation setup), from all the excitation setups available to the apparatus, to apply RF energy to zone 102. Controller 150 may select a subgroup of excitation setups based on the RF feedback received at each excitation setup or at one or more excitation setups.

In some embodiments, when RF energy is applied to process the object, the controller may be configured to determine amounts of RF energy to be applied at each excitation setup (e.g., associate RF energy amounts with each of the excitation setups), for example—based on the RF feedback. In certain embodiments, the controller may be configured to determine, from at least a part of the RF feedback, an absorbability indicator, (or in short, AI) at each of a plurality of excitation setups in which energy is applied to the zone. The controller may be configured to associate RF energy amounts with each of the excitation setups available for an apparatus based on the AI value at the respective excitation setup. The rules in which the controller may cause the application of RF energy to the energy application zone based on the RF feedback (e.g., the AI) may be included in one or more scripts for applying RF energy to process an object. For example, a script or a rule may include a decision not to supply RF energy to excitation setups associated with certain AI values, for example, those that may have AI values lower than a minimum threshold and/or higher than a maximum threshold. In other examples, the script or the rule may include, associating the same amount of RF energy with excitation setups associated with different AI values, for example, with values in a certain range. Additionally or alternatively, according to another script, the controller may associate different amounts of RF energy with excitation setups associated with different AI values. In some embodiments, other rules or scripts based on the AI values and/or other RF feedback may be utilized by the controller for determining the amounts of RF energy to be applied for processing the object.

Applying RF energy to the zone, to either detect a processing state of the object and/or heat the object, may be done by a sweep, and RF feedback may be received and associated with different excitation setups during the sweep. As used herein, a sweep may include, for example, the application, over time, of energy at more than one excitation setup. For example, a sweep may include the sequential application of energy at multiple excitation setups in one or more contiguous excitation setup group; the sequential application of energy at multiple excitation setups in more than one non-contiguous excitation setup group; the sequential application of energy at individual non-contiguous excitation setups; and/or the application of synthesized pulses having a desired excitation setup/power spectral content (e.g., a synthesized pulse in time). The excitation setups groups may be contiguous or non-contiguous. Thus, during an excitation setup sweeping process, one or more controllers may regulate the energy supplied from a source (e.g., source 112) to one or more radiating elements to sequentially apply RF energy at various excitation setups to zone 102 (e.g., by switching from one c-FAP to the other) and to receive RF feedback from zone 102 associated with each excitation setup.

During the sweeping process, controller 150 may receive raw RF feedback indicative of the energy reflected and/or coupled at radiating elements 110, 120 and 130. Controller 150 may then determine an absorbability indicator (AI) by object 103 (i.e., a computed RF feedback) at each of a plurality of excitation setups based on the received information. Consistent with some disclosed embodiments, an absorbability indicator (AI) may include a dissipation ratio (DR) associated with each of a plurality of excitation setups. As referred to herein, a DR (or absorption efficiency or power efficiency) associated with an emitting radiating element may be defined as a ratio between EM energy absorbed by object 103 and EM energy supplied into the energy application zones by the emitting radiating element. In some embodiments, a DR may be defined as a ratio between EM energy absorbed by object 103 ('AE') and EM energy delivered by the emitting radiating element ('DE'). Some examples for computed RF feedback (e.g., DR) are given below.

In some embodiments, a DR associated with an emitting radiating element (e.g., element 110) may be calculated using Equation (3):

$$DR=AE/SE \qquad (3)$$

wherein SE is the energy supplied by source 112 to emitting radiating element 110 and AE is the energy absorbed, for example in object 103. Both SE and AE may be calculated by integrating over time of power detected by power detectors (e.g., detectors 118, 118a, 128 or 138). For t=ti, wherein ti may be any moment in time during which energy is applied to the energy application zone, equation (4) may have the form:

$$DR=P_A/P_S; \qquad (4)$$

Wherein $P_A$ is the power absorbed and $P_S$ the power supplied from the RF source. $P_A$ may be evaluated using equation (5):

$$P_A=P_S-P_{out}; \qquad (5)$$

wherein $P_{out}$ refers to the power detected by all the detectors (e.g., radiating elements 120 and 130 act as receiving radiating elements), denoted as $P_{detect}(i)$ in the $i^{th}$ detector, in and around the energy application zone, when $P_S$ was supplied to radiating element 110, from RF source 112 at a certain excitation setup, see equation (6):

$$P_{out}=\Sigma P_{detect}(i) \qquad (6)$$

If the only available detectors are the ones associated with the radiating elements (e.g., detectors 128 and 138 associated with radiating elements 120 and 130 respectfully), DR may be calculated using three detected power parameters $P_S$, $P_R$ and $P_C$ and equation (6) may have the form of equation (7):

$$DR=(P_S-P_R-P_C)/P_S \qquad (7)$$

where $P_S$ represents the RF power supplied to emitting radiating element 110, $P_R$ represents the EM energy and/or power reflected/returned to the emitting radiating element 110, and $P_C$ represents the EM energy coupled to the other radiating elements (e.g., 120 and 130) function as receiving elements. DR may be a value between 0 and 1, and thus may be represented by a percentage number.

For example, consistent with an embodiment which is designed for three radiating elements 110, 120, and 130, controller 150 may be configured to determine raw RF feedback parameters, such as the input reflection coefficients $S_{11}$, $S_{22}$, and $S_{33}$ and transfer coefficients $S_{12}$, $S_{21}$, $S_{13}$, $S_{31}$, $S_{23}$, and $S_{32}$ based on measured power and/or energy information during the sweep.

Accordingly, the computed RF parameter (DR) corresponding to radiating element 1 may be calculated based on the above raw RF feedback parameters (e.g., the reflection and transmission coefficients (a/k/a S parameters)), according to equation (8):

$$DR_1 = 1 - (|S_{11}|^2 + |S_{12}|^2 + |S_{13}|^2) \tag{8}$$

As shown in equation (8), DR may be different at different radiating elements. Thus, in some embodiments, an amount of energy supplied to a particular radiating element may be determined based on the AI associated with that particular radiating element.

During the EM energy application, additional computed RF feedback may be calculated and monitored based on the DR. In some embodiments, an average DR, for example, averaged over all transmitted excitation setups (ES), may be calculated. For example, an average DR may optionally be calculated for each radiating element, as a function of time, using equation (9):

$$\overline{DR} = \frac{1}{N} \sum_i DR(ES_i) \tag{9}$$

Wherein $DR(ES_1)$ is the dissipation ratio measured when the RF energy was supplied using the $i_{th}$ excitation setup, and i is an integer between 1 to N wherein, N is the number of excitation setups used to apply energy to the energy application zone in a particular application. The average DR may vary over time. In some embodiments, the computed RF feedback may include ES average of other RF feedback, for example raw RF parameters (e.g., the reflection and transmission coefficients).

In some embodiments, DR (or a different absorbability indicator) calculated for an excitation setup may be time dependent. RF feedback received at that excitation setup may be monitored at different occasions during the energy application (during processing) and DR (or any other computed RF feedback used for determining amounts of energy to be supplied (e.g., temperatures, power levels, durations of energy application etc.)) may be calculated at each occasion. Thus equations (7) and (8) may take the form:

$$DR(t) = (P_S(t) - P_R(t) - P_C(t))/P_S(t) = 1 - (|S_{11}(t)|^2 + |S_{12}(t)|^2 + |S_{13}(t)|^2) \tag{7,8}$$

Additionally or alternatively the average DR may time dependent. Thus an average over N excitation setups as a function of time is presented in equations (10):

$$\overline{DR(t)} = \frac{1}{N} \sum_i DR(t)(ES_i) \tag{10}$$

In some embodiments, the average DR may be correlated with one or more processing states of the object (e.g., the temperature of the object, the cooking state of the object, etc.). The average DR may be monitored during cooking (e.g., during baking) and the cooking state of the object may be determined based on the average DR. The correlation may be done, for example, by using a lookup table stored in memory associated with apparatus 100, comprising threshold values of the computed RF feedback (e.g., the average DR) and comparing the average DR received from the energy application zone during processing.

In some embodiments, the correlation between average DR and a processing state of the object may be recorded in a memory (e.g. in a lookup table, or any other suitable format). For example, as the object is being processed, a processing state of the object may be determined based on RF feedback received from the object, based on input from a user, based on automated monitoring devices (IR sensors, thermometers, cameras, or any other type of sensor or detector configured to monitor at least one property or characteristic of the object being processed), or based on any other input from a monitoring source. The processing state of the object may then be correlated with an average DR determined for the object at various (e.g., periodic) times during processing. This correlated information may be stored.

In some embodiments, correlated average DR and processing state information stored in a memory may be accessed and used in processing objects. For example, to process a particular object, the controller may access a memory (either remotely located or local to the controller) and identify stored information for the same or similar type of object. The controller may then rely upon the stored information, either fully or partially, to process the particular object. That is, rather than having to monitor the processing state of the object through separate input from sensors or detectors, the controller may determine the processing state of the object by monitoring an average DR obtained from the particular object during processing, accessing the information stored in memory, and determining a processing state of the object based on the observed average DR and the stored correlation between average DR and processing state of a same or similar type of object.

In some embodiments, a time average of DR may be calculated while giving different weights to different excitation setups. When plotting each of the DR(t)(ES) versus time, some of the plotted curves may show variation in the value of DR over time (the time derivative of DR(ESi) may be higher than a threshold). In some embodiments, the average DR may be calculated assigning more weight to DR(t)(ES) having larger variations than to DR(t)(ES) having lower variations (the time derivative of DR(ESi) may be lower than a threshold). In some embodiments, DR(t)(ES) having lower variations may be assigned with a zero weight. For example, the weighted average $\overline{DRw}$ may be calculated using equation (11):

$$\overline{DR_w(t)} = \Sigma_i w_i \cdot DR(ES_i)(t) \tag{11}$$

wherein $w_i$ is the weight given to $DR(ES_i)(t)$.

In certain embodiments, the average DR may be calculated over time for each excitation setup.

In some embodiments, a reflection coefficient $\Gamma$ may be used as an absorbability indicator of the object. This AI may be defined by equation (12):

$$\Gamma = \frac{\sum SE - \sum RE}{\sum SE} \tag{12}$$

where $\Sigma SE$ represents the sum of all amounts of energy (or power) supplied to emitting radiating elements, and $\Sigma RE$ represents the sum of all amounts of energy (or power) received by the emitting radiating elements. The reflection coefficient Γ may be used when more than one emitting radiating element emit RF energy simultaneously.

In some embodiments, processing of the object may be automatically controlled based on one or more raw or computed RF feedback (e.g., DR and/or average DR). Energy may be applied to process the object using one or more energy application protocols. The protocols may include at least one of: the type of energy to be applied (e.g., convection heating, IR heating or RF heating), the amount of energy to be applied (e.g., the temperature, the power levels, amount of RF energy) and the duration of the application of each type of energy. The different protocols may be predetermined and stored in a memory associated with controller 150, or on a machine readable element associated with the object. Controller 150 may be configured to select an energy application protocol to be applied to process the object based on RF feedback received from the energy application zone. Additionally or alternatively, the controller may be configured to terminate the energy application and/or switch to another energy application protocol based on the received RF feedback and/or computed RF feedback. For example, the RF feedback may be detected during the application of energy according to a first energy application protocol, and when a value of an RF feedback (e.g., the DR(t), the average DR(t) or time derivatives of the DR(t), and/or the average DR(t)) reaches a target value, the energy application may stop or change in at least one aspect (e.g., to a second energy application protocol). For example, the application of convection heating for baking a loaf of bread may be terminated. Additionally, processing of the object may be controlled based on one or more other feedbacks (e.g., signals received from one or more sensors, e.g., sensor 140, provided in the energy application zone). Additionally, processing of the object may be controlled by processing instructions provided by a user, e.g., by a graphical user interface (GUI) or instructions read from a machine readable element associated with the object. The instructions may be configured to cause the at least one controller (e.g., controller 150) to control the energy application to process the object.

In certain embodiments, when the energy applied to process the object includes RF energy, controller 150 may determine an RF energy application protocol by adjusting the amount of RF energy supplied at each excitation setup based on the RF feedback (e.g., RF feedback parameters). RF feedback may be received from energy application zone 102, e.g., during sweeping over a plurality of excitation setups. For example, according to some embodiments, controller 150 may be configured to determine the amount of energy to be supplied at each excitation setup based on RF feedback received at the respective excitation setup. An energy application protocol may be selected to include an amount of energy determined based on RF feedback. In some embodiments, an energy application protocol may dictate that amounts of energy applied at some excitation setups may be inversely related to the RF feedback values at these excitation setups (e.g., AI(ES)) calculated for the respective excitation setups. Additionally or alternatively, an energy application protocol may dictate that amounts of energy applied at an excitation setup have an inverse relationship with another RF feedback. RF feedback related values may include any value of RF feedback that may be received during the application of RF energy at a particular excitation setup. Additionally or alternatively, an amount of energy associated with a particular energy application protocol for application at an excitation setup may be determined according to other relationships. For example, a linear relationship between energy applied and feedback-related values may be used to determine an amount of energy to apply. For example, when the AI in a particular excitation setup subgroup (i.e., one or more excitation setups) tends to be relatively high (e.g., above a predetermined threshold or higher than the average AI value over a set of excitation setups that includes the subset, etc.), the amount of energy determined by an energy application protocol to be applied at each excitation setup of that excitation setup subgroup may be relatively low (e.g., lower than the amounts of energy applied at any excitation setup associated with AI values below the predetermined threshold). Additionally or alternatively, when an indicator of absorbable energy in a particular excitation setup subgroup tends to be relatively low (e.g., below a predetermined threshold or below the average AI value over a set of excitation setups that includes the subset, etc.), the applied energy may be relatively high (e.g., higher than the amounts of energy applied at any excitation setup associated with AI values above the predetermined threshold). According to some energy application protocols, there may be a substantially inverse relationship between the amounts of energy applied at different excitation setups and the AI values calculated for the same excitation setups. In some embodiments, if the energy applied according to such protocols at each excitation setup is plotted against the AI value calculated for the excitation setup at which energy is applied, the resulting line may include a decreasing line segment. In some embodiments, the decreasing line segment may have a constant slope. In other embodiments, the slope of the decreasing line segment may vary. In some embodiments, the slope may vary such that a multiplicative product of the AI value and amount of energy applied remains substantially constant.

Controller 150 may be configured to hold substantially constant the amount of time at which energy is supplied to radiating elements 110, 120 and 130 at each excitation setup, while varying the amount of power supplied at each excitation setup as a function of the absorbable energy value. In some embodiments, controller 150 may be configured to cause the energy to be supplied to radiating element at a particular excitation setup or excitation setups at a power level substantially equal to a maximum power level of the device and/or the amplifier at the respective excitation setup(s). Alternatively or additionally, controller 150 may be configured to vary the period of time during which energy is applied at each excitation setup as a function of the absorbable energy value. In some embodiments, both the time duration and power at which each excitation setup is applied are varied as a function of the absorbable energy value.

Controller 150 may be further configured to control the RF energy application by controlling various aspects of the energy application units (e.g., units 119 and 119a) and RF energy source (e.g., sources 112, 122 and 132).

In some embodiments, apparatus 100 may include a phase modulator (not illustrated) that may be controlled to perform a predetermined sequence of time delays on an AC waveform, such that the phase of the AC waveform is increased by a number of degrees (e.g., 10 degrees) for each of a series of time periods. The time delays may be considered c-FAPs in apparatus 100. In some embodiments, controller 150 may dynamically and/or adaptively regulate modulation based on feedback (e.g., RF feedback—for example, AI) from the energy application zone. In some embodiments, controller 150 may select phases (between pairs of radiating elements) based on the EM feedback (e.g., the absorbable energy value).

In some embodiments, apparatus 100 may include a frequency modulator (not illustrated). The frequency modulator may include a semiconductor oscillator configured to generate an AC waveform oscillating at a predetermined frequency (i.e., the frequency is a c-FAP in this apparatus). The predetermined frequency may be associated with an input voltage, current, and/or other signal (e.g., analog or digital signals). For example, a voltage controlled oscillator may be configured to generate waveforms at frequencies proportional to the input voltage.

Controller 150 may be configured to regulate an oscillator (not illustrated) to sequentially generate AC waveforms oscillating at various frequencies within one or more predetermined frequency bands. This sequential process may be referred to as frequency sweeping. In some embodiments, based on the feedback signal provided by detector 118, controller 150 may be configured to select one or more frequencies from a frequency band, and regulate an oscillator to sequentially generate AC waveforms at these selected frequencies. In some embodiments, the frequencies may be selected based on the EM feedback (e.g., the absorbable energy values).

In some embodiments, the energy application unit (e.g., unit 119a included in FIG. 1B) may include more than one source of RF energy. For example, more than one oscillator may be used for generating AC waveforms of differing frequencies. The separately generated AC waveforms may be amplified by one or more amplifiers. Accordingly, at any given time, radiating elements may be caused to simultaneously emit RF waves at, for example, two or more differing frequencies (i.e., two different c-FAPs) to zone 102.

In some embodiments, a splitter (not illustrated) may be provided in apparatus 100 to split an AC signal e.g., a signal generated by an oscillator) into two AC signals (e.g., split signals). Controller 150 may be configured to regulate a phase shifter to sequentially cause various time delays such that the phase difference between two split signals may vary over time. This sequential process may be referred to as phase sweeping.

In some embodiments, apparatus 100 may include at least one interface 160 (for example, as illustrated in FIG. 1A or FIG. 1B). Controller 150 may be configured to receive from interface 160 one or more processing instructions and/or other information related to the object. Interface 160 may include any user interface, e.g., a GUI, a touch screen, a key pad, a screen associated with a mouse, etc. A first interface may be configured to receive from a user an indication of a processing state of the object. For example, the user may indicate to the controller via the first interface that a food item has being cooked to a desired degree of doneness or reached a desired level of browning. In some embodiments, a second user interface 160 may be configured to display to a user a representation indicative of the processing state associated with the object (i.e., an image associated with the RF feedback). For example: one or more signals of sensor 140—e.g., the temperature of the object while processing may be displayed as graphs. In some embodiments, a single interface (e.g., one display) may be used both to display to a user one or more signals of sensor(s) and to receive inputs from the user. In some embodiments, user interface 160 may be configured to display to a user one or more RF feedback and/or computed RF feedback while processing the object. Additionally or alternatively, a third interface 160 may include a device capable of reading and receiving information (e.g., protocol(s)) from a machine readable element, for example a barcode reader, an RFID reader, etc. Controller 150 may be configured to receive the energy application protocol solely based on the information received from interface 160 or in combination with the RF feedback. In some embodiments, the first and/or second and/or the third user interfaces are the same. Additionally or alternatively, controller 150 may be configured to determine the energy application protocol solely based on user instruction received from interface 160, e.g., a user may instruct processing information through a GUI. For example, the controller may receive from the interface (e.g., from a machine readable element or from a user) a target value (i.e., a criterion) of the RF feedback (e.g., a time derivative of the average DR value) and the controller may monitor the RF feedback during the processing and terminate the processing of the object when the RF feedback reaches the target value (i.e., the criterion).

In some embodiments, the user interface may include a display (not illustrated) and the controller may be further configured to display to a user the monitored RF feedback and/or a representation indicative of the processing state associated with the object. The user may then decide based on the displayed RF feedback or processing state, how to control the energy application to the object. The display may include any screen configured to display a visual representation to a user either graphically or by any other technique. Additionally or alternatively, the display may include an audio system configured to provide an audio representation for the user.

In some embodiments, the user may create a machine readable element (e.g., a barcode) based on the information provided to the user (e.g., displayed) by interface 160, for example: based on the RF feedback and/or computed RF feedback, one or more signals of sensor(s) 140, and or correlation thereof. In some embodiments, the energy application protocol used and/or the RF feedback (e.g., its value(s)) correlated with one or more processing states to obtain a desired result may be recorded by the user and used for creating the machine readable element or used for future processing of the same or similar object (e.g., for automatic cooking)—for example: it may be used to create a special program in the interface for obtaining a specific result when processing the object.

Figure 2B:
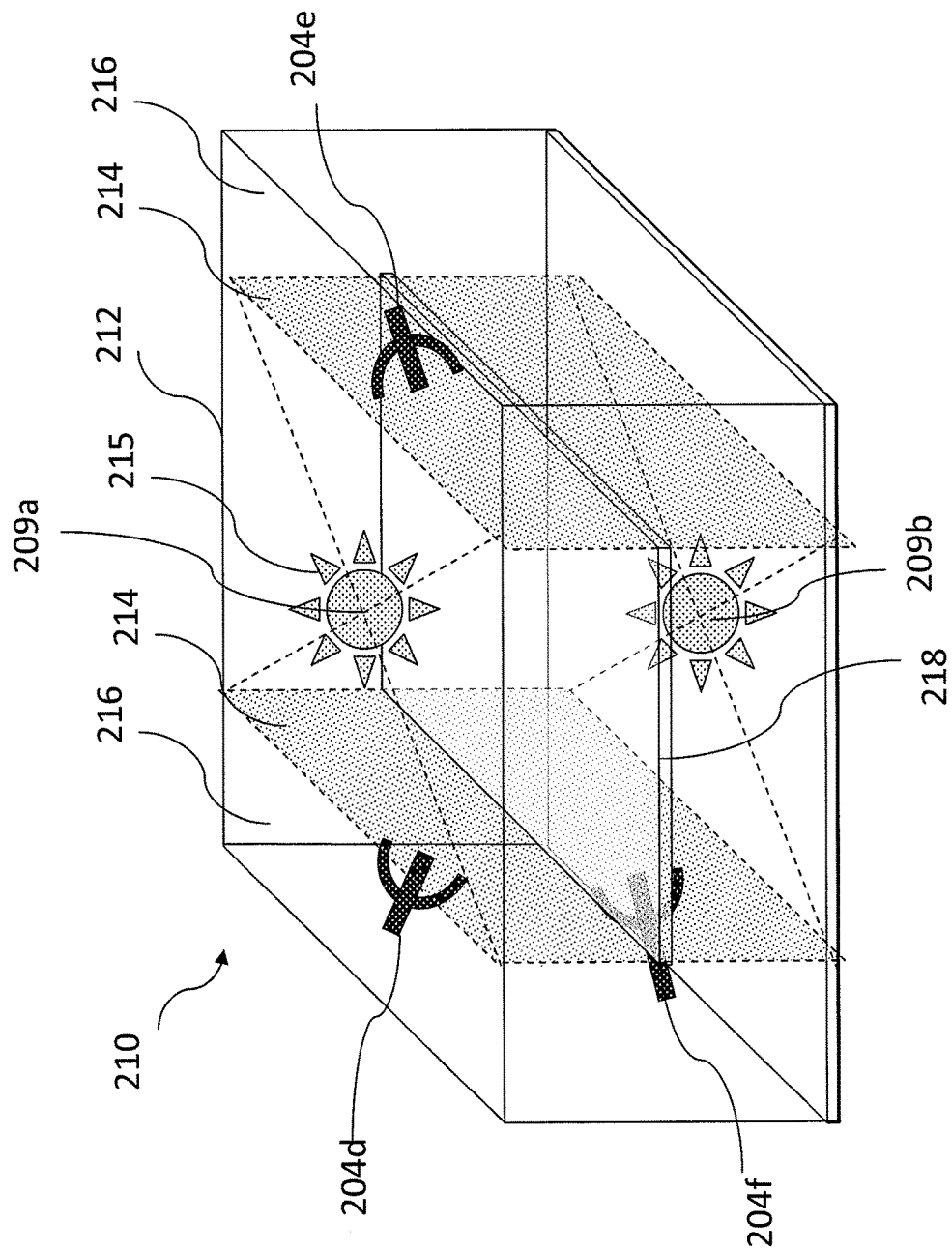

Reference is now made to FIGS. 2A-2B which illustrate some exemplary cavities in accordance with some embodiments of the invention. In some embodiments, the energy application zone may be at least partially located inside a cavity. Cavities 200 and 210 may be exemplary energy application zones and may be part of apparatus 100. A cavity may include any void comprising at least one wall made from a material substantially opaque to RF energy. Any of the walls of a cavity may be made from materials opaque to RF energy. For example, an oven may be constructed from cast iron, stainless steel, or aluminum alloys or other metals and alloys suitable for constructing a cavity. Alternatively, the at least one wall may comprise a dielectric material at least partially transparent to RF energy and coated by a coating made from material substantially opaque to RF energy. A material substantially opaque to RF energy may include any material capable of blocking or reflecting RF energy above a predetermined threshold (e.g., above 90%).

FIG. 2A includes a diagrammatic representation of a cavity 200 in accordance with some embodiments. Cavity 200 may include cavity body 202. Cavity body 202 may be configured to hold at least a portion of an object (e.g., object 103). Cavity body 202 may comprise at least one wall constructed from or coated by, a material substantially opaque to RF energy. Cavity body 202 may have a rectangular shape (as illustrated), cylindrical shape, or may have any other suitable shapes. For example, cavity body 202 may take a shape of a cooking oven for cooking food, a cylindrical tank for processing liquids, an industrial furnace for curing polymers or sintering parts, a pipe comprising flowing fluids and/or gasses, etc. Cavity 200 may further comprise at least one radiating element. For example, cavity 200 may include three (or more) radiating elements 204a, 204b, and 204c as illustrated in FIG. 2A. Any or all of radiating elements 204a, 204b, or 204c may constitute examples consistent with any of the radiating element described herein. Radiating elements 204a, 204b, and 204c may include any elements configured to emit and/or receive RF energy from the cavity (e.g., to detect a processing state of the object). The radiating elements may be connected to an RF source (e.g., source 112 illustrated in FIG. 1B), to a detector configured to detect one or more RF feedback (e.g., detector 118a in FIG. 1B) and to a controller (e.g., controller 150 in FIG. 1B). Radiating elements may be installed in proximity to at least one cavity wall (for example, element 204a). A radiating element may be installed outside the cavity (for example, element 204b), in proximity to a cavity wall having an RF transparent window 205. RF transparent window 205 may be constructed from any dielectric material capable of transferring at least a portion of the RF energy emitted from element 204b to cavity 200. A radiating element may be located in proximity to or at least partially inside object 103 (for example, element 204c). For example, element 204c may be immersed in a solution in a chemical reactor or a beer in a brewery tank, element 204c may also be embedded in a filter or a catalytic convertor in order to heat the filter or the convertor. In some embodiments, radiating elements 204a, 204b, and 204c may be part of one or more energy application units (not illustrated)—(e.g., unit 119 or 119a).

In some embodiments, cavity 200 may include at least one sensor, such as sensors 206 and 208, which may be similar to sensor 140 described above. Sensors 206 and 208 may constitute exemplary processing state indicators. Sensor 206 may be embedded in, immersed in or placed in proximity to object 103. Sensor 206 may include any sensor configured to measure a property (e.g., an indication of the processing state) of object 103. The property may include a measurable property, such as temperature, pressure, volume, pH, humidity ratio, density, moisture, etc. Additionally or alternatively, the property may include other characteristics, such as color, taste, doneness, smell, etc. In some embodiments, one or more properties may be monitored (e.g., detected) by sensor 206. In some embodiments, sensor 206 may be configured to measure RF feedback (e.g., raw RF feedback parameters) detected in cavity 200. For example, sensor 206 may be configured to measure the intensity of the EM field excited in cavity 200 by the radiating element(s). In some embodiments, sensor 208 may be installed in proximity to or on at least one wall in cavity 200. Sensor 208 may include any sensor configured to measure a property (e.g., an attribute, condition, etc. indicative of the processing state) of object 103 or cavity 200. Similar to sensor 206, sensor 208 may sense one or more properties associated with object 103 and/or the surrounding environment of the object. In some embodiments, sensors 206 and 208 may be configured to sense the same or similar properties. In some embodiments, sensors 206 and 208 may sense different properties. For example, sensor 206 may sense the temperature of the object, and sensor 208 may sense humidity in cavity 200 in the vicinity of object 103. Sensors 206 and 208 may be in communication with a controller (e.g., controller 150). In some embodiments, processing of the object (e.g., energy application) may be controlled in accordance with one or more signals sensed by sensor 206 and/or 208.

In some embodiments, cavity 200 may further include at least one energy (heat) source 209. Source 209 may be configured to apply energy (e.g., heat) to cavity 200 to process object 103. Source 209 may include any convection heating source, for example: a filament, hot air impingement, gas flame, or any other heating element configured to apply heat to an object by convection means. Additionally or alternatively, source 209 may include IR lamp configured to apply IR radiation to object 103. In some embodiments, energy may be applied to process the object from two different sources. For example, source 209 may apply heat (convection or IR) and at least one of radiating elements 204a, 204b and/or 204c may apply RF energy to process the object as well and/or to detect a processing state of the object by receiving RF feedback from the object. Source 209 may apply the energy (e.g., heat), and the at least one radiating element may additionally apply RF energy to process the object, simultaneously, consecutively, or a combination of both. Alternatively, energy for processing the object may be applied solely from source 209, and the radiating elements may apply RF energy to detect the processing state of the object.

FIG. 2B illustrates an exemplary cavity according to some embodiments of the invention. Cavity 210 may include, for example, one or more of the components shown in FIG. 2A. Cavity 210 may include cavity body 212. Cavity body 212 may comprise at least one wall constructed from a material substantially opaque to RF energy. Cavity 210 may have any shape or size allowing holding of at least a portion of an object. Cavity 210 may further include at least one radiating element configured to emit and/or receive RF energy from cavity body 212, optionally more than one radiating element (e.g., 3 elements 204d, 204e and 204f may be installed in cavity 210. Each of elements 204d, 204e and 204f may be connected to a detector (e.g., detector 118a illustrated in FIG. 1B) and may be in communication with a controller (e.g., controller 150) configured to receive signals related to RF feedback from the detectors connected to elements 204d, 204e and 204f. Radiating elements 204d, 204e, and 204f may be part of one or more energy application units (not illustrated)—(e.g., unit 119 or 119a). The RF feedback (e.g., computed RF feedback) received from elements 204d, 204e and 204f, may be indicative of a processing state of the object. Elements 204d, 204e and 204f may be located on or in proximity to cavity body 212 walls. Each element may be located on a different wall. Additionally or alternatively, more than one radiating element may be located on the same wall. The invention is not limited to any particular radiating elements configuration. Elements 204d, 204e and 204f may be any radiating elements according to the embodiments of the invention (e.g., elements 110, 111 etc.). Elements 204d, 204e and 204f may be located in volume 216 between cavity body 212 walls and at least one partition 214. Optionally, more than one partition 214 (e.g., 2 partitions illustrated in FIG. 2B) may be installed in cavity 210. Partitions 214 may be constructed from a material at least partially transparent to RF energy. Additionally or alternatively, at least one partition 214 may include at least one window consisting of a material at least partially transparent to RF. Some examples of materials transparent to RF energy may include: various glasses, polymers and some ceramics and their composites. Partitions 214 may separate inner volume 215 and one or more radiating elements 204d, 204e and 204f. Elements 204d, 204e and 204f may be installed in at least one outer volume 216. Inner volume 215 may be configured to hold at least a portion of an object (e.g., object 103) and partitions 214 may be configured to separate the object from the radiating elements. In some embodiments, the energy application zone may be located at least partially within inner volume 215. For example, if the object is a meat or chicken to be cooked, partitions 214 may protect elements 204d, 204e and 204f from water and oil vapors extracted from the meat or the chicken during cooking. In yet another example, the object may include a chemical solution to be reacted, and inner volume 215 may be a chemical reactor. Thus, partitions 214 may protect elements 204d, 204e and 204f from a corrosive attack by the chemical solution.

In some embodiments, cavity 210 may further include tray 218. Tray 218 may be located in volume 215, separating volume 215 into two parts each capable of holding different object(s). Tray 218 may be at least partially transparent to RF energy, allowing at least a portion of the energy applied from the two upper radiating elements 204d and 204e to enter the lower part of cavity 210 and vice versa with respect to the lower radiating element 204f. Tray 218 may comprise a heat resistant polymer, for example Silicone, Teflon, etc. Tray 218 may comprise glass (e.g., tempered soda-lime glass also known as Pyrex) or ceramic material. Tray 218 may be substantially opaque to RF energy, blocking much or all of the RF energy emitted from elements 204d and 204e from enter the lower part of cavity 210, and vice versa. Tray 218 may comprise any metallic material, including, for example, various stainless steels, cast iron, aluminum based alloys, cupper based alloys etc.

In some embodiments, cavity 210 may further include one or more energy (heat) sources 209a and 209b, similar to source 209 illustrated and disclosed in respect to FIG. 2A. Source 209b may be located to apply energy (e.g., heat) to the lower portion of volume 215, and source 209a may be located to apply energy (e.g., heat) to the upper portion of volume 215. In some embodiments, energy may be applied to process object(s) placed in either or both portions of volume 215, from sources 209a and 209b, and RF energy may be applied from radiating element 204d, 204e and 204f (e.g., to process (heat) the object and/or to detect processing state(s) of the object).

Figure 3A:
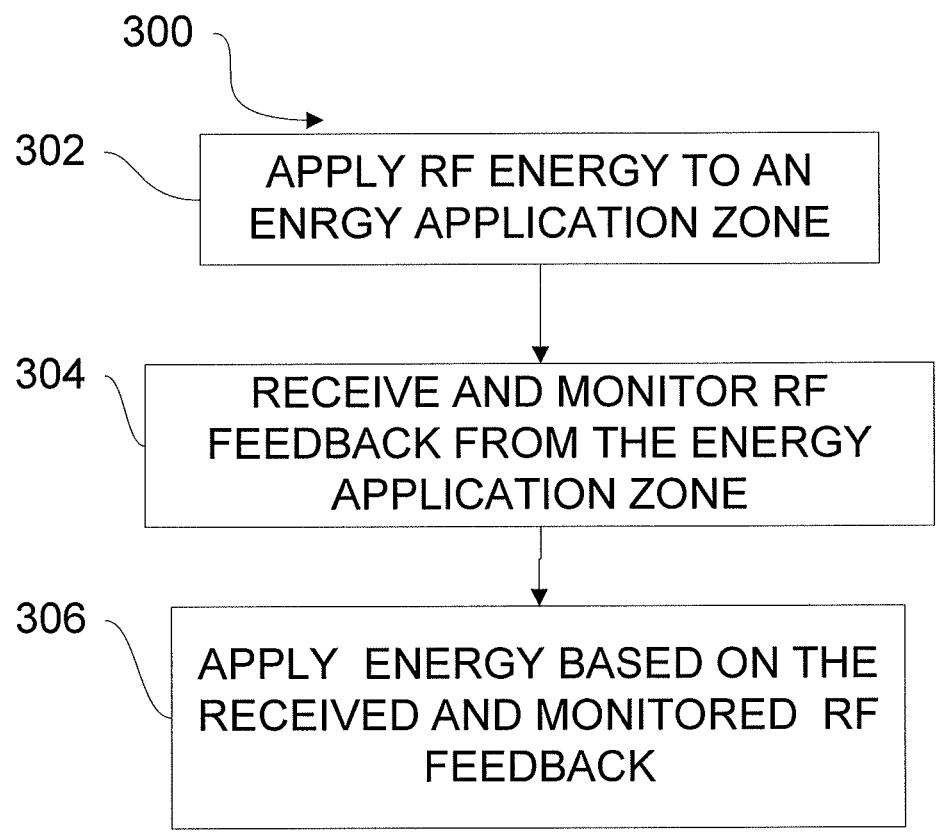
FIGS. 3A and 3B include flowcharts of two methods for controlling energy application to an energy application zone based on RF feedback, in accordance with some embodiments of the invention.
Figure 3B:
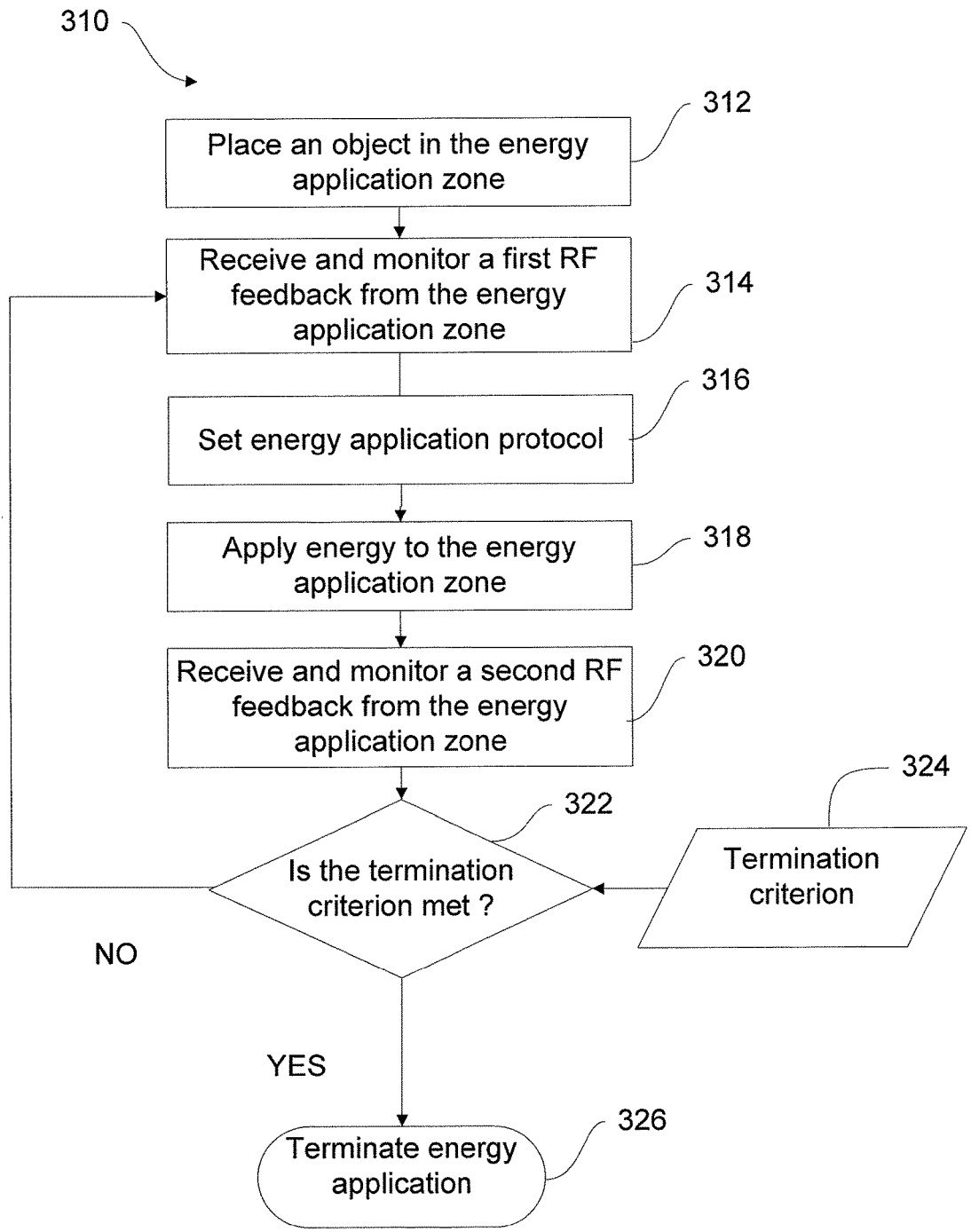

Method 300 for controlling energy application to an energy application zone based on RF feedback in accordance with some embodiments of the invention is presented in the flowchart in FIG. 3A. Method 300 may include applying RF energy to an energy application zone, to detect a processing state of an object placed in an energy application zone, during processing of the object. Method 300 may be performed by controller 150, using apparatuses 100. RF energy may be applied to the energy application zone (e.g., zone 102 and cavities 200 and 210), in step 302, via one or more radiating elements. The RF energy may be applied, during the processing of the object, in order to detect RF feedback (e.g., computed RF feedback). RF energy may be applied at one or more excitation setups. The RF energy may be applied for example every 1 second, 3 seconds, 5 seconds or 10 seconds, or other periods of time. The object may be processed by applying energy (e.g., in convection or IR). In some embodiments, low amounts of RF energy may initially be applied at one or more excitation setups. Low RF amounts of energy may be defined as amounts of energy applied to the energy application zone that result in little or no processing of an object (e.g., object 103) placed in the zone. For example, the low amounts of energy may not be sufficient to: cook a food item, thaw frozen object, cause or accelerate chemical reaction, etc. Low amounts of energy may be applied by for example, by applying low RF power from the RF source (e.g., source 112) or by applying high power for very short period of time. Alternatively, RF energy application in step 302 may be conducted at energy levels sufficient to process an object placed in the energy application zone by a certain degree. The RF energy application in step 302 may be conducted by sweeping over a plurality of excitation setups available in apparatus 100 (e.g., at a plurality of frequencies), for example, by transmission over time of energy at more than one excitation setup. A controller (e.g., controller 150) may control the RF energy application by sweeping over a plurality of excitation setups and assigning a constant (e.g., low) amount of energy to be applied at each excitation setup.

The controller may then receive or detect, and optionally monitor, RF feedback from the energy application zone, in step 304. The RF feedback may be detected (received) in response to the RF energy application. The RF feedback may include a result of the RF energy applied in step 302. The RF feedback may be received from one or more sensors and/or detectors configured to measure raw RF feedback in the energy application zone optionally at each of the applied excitation setup. The received raw RF feedback may be processed to determine a computed RF feedback—for example by conducting mathematical manipulation of raw RF feedback parameters or values received from the energy application zone, for example: the computed RF feedback may include: a DR, an average DR, a time derivative of any of the signals, etc. The computed RF feedback may be correlated with one or more processing states of the object. Method 330 for recording (e.g., on a memory associated with controller 150 or on a machine readable element) a correlation between an RF feedback value (or a computed RF feedback) and a processing state of an object is disclosed in FIG. 3C. The correlation recording may be done during heating of an exemplar of the object (e.g., object 103) being heated. The exemplar object may comprise at least some of the characteristics of the heated object. Thus when an RF feedback and an indication of a processing state of an object is correlated and recorded during heating experiments of the exemplar object, the recorded correlation may be used to control energy application to the object (e.g., object 103).

In some embodiments, the computed RF feedback may be monitored to detect a processing state of the object, for example by comparing the recoded correlation (e.g., stored as a look up table) and the received computed RF feedback (e.g., one or more values of the computed RF feedback). The controller (e.g., controller 150) may monitor at least one computed RF feedback parameter (e.g., DR, average DR, time derivative off, etc.) before, during or after processing (e.g., heating) of the object. The controller may compare the at least one monitored computed RF feedback parameter (e.g., its value) with a correlated computed RF feedback (value) recorded and stored for example in a lookup table. The correlation received may be used to determine the one or more processing states of the object. The correlation may be recorded and stored on a memory associated with the controller or on a machine readable element associated with the object and the controller may be configured to receive the correlation between the RF feedback and the processing state of the object from the memory and/or the machine readable element. The correlated computed RF feedback (e.g., one or more values) may be collected during processing of another object that may be representative to the object processed.

The raw RF feedback may be sensed or detected every 1 second, 3 seconds, 5 seconds or 10 seconds, or at any other desired time period. Various RF feedbacks may be received by the controller during the application of RF energy at various excitation setups, for example, during sweeping over a plurality of excitation setups. The controller may be configured to associate some or all of the RF feedback (e.g., its values) with a corresponding excitation setup. In some embodiments, when detected before processing begins—the computed RF feedback received in step 304 may be indicative of the initial state of the object. An exemplary initial state of the object may comprise a frozen object, a deeply frozen (e.g., below a threshold temperature) object, an object at room temperature or in general the initial temperature of the object before processing, different defrosting states, volume of an object, number of pieces or items associated with the object or objects, the position of each item in a package, etc.

In some embodiments, the RF feedback (e.g., the computed RF feedback) may be correlated with one or more processing states of the object. The correlation may be determined in accordance with method 330. In some embodiments, the controller may detect one or more processing states of the object based on the monitored RF feedback (e.g., the computed RF feedback). The controller may display or otherwise provide the detected processing state(s) to the user (e.g., via interface 160). In some embodiments, the user may provide instructions configured to cause the at least one processor to process the object based on the provided processing state(s).

In step 306, the controller may control the processing of the object by applying energy based on the received and optionally monitored RF feedback. For example, the controller may cause application of energy when the computed RF feedback values received from the energy application zone include values lower or higher than a threshold. Additionally or alternatively, when the object is processed by RF energy, the controller may adjust the RF energy amounts applied at each excitation setup as a function of the computed RF feedback at that excitation setup. In some embodiments, the controller may terminate the process when the computed RF feedback (its value) reached or is below a predetermined threshold.

In some embodiments, the process may repeat and RF energy may be applied to detect the processing state of the object during and/or after the energy application. Steps 302 and 304 may be repeated and the processing may be re-adjust in step 306 based on the computed RF feedback received in step 304. In some embodiments, steps 302 and 304 may be performed several times while processing the object—e.g., every 3 or 5 seconds.

In some embodiments, an energy application protocol may be set based on the RF feedback (e.g., a computed RF feedback) received from the energy application zone. Method 310 presented in the flowchart in FIG. 3B may comprise placing an object (e.g., object 103) in an energy application zone (e.g., zone 102), in step 312. Method 310 may be performed by controller 150, using apparatuses 100. RF energy may be applied to the energy application zone to detect a processing state of the object by receiving and monitoring a first RF feedback (e.g., computed RF feedback) for example, by controller 150, in step 314. The RF feedback received in step 314 may be indicative of the initial state of the object. In some embodiments, the detected initial state may be displayed to the user (e.g., through an interface). The RF energy may be applied at a plurality of excitation setups, for example, by sweeping over at least a portion of available excitation setups, and the RF feedback may be received and associated with each of the applied excitation setups, as disclosed above with respect to steps 302 and 304 in method 300. The received RF feedback (e.g., one or more values or trend—for example: when the value changes from increasing to decreasing over time) may be correlated with one or more processing states of the object as discussed above.

Based on the received first RF feedback, a controller (e.g., controller 150) may set or determine an energy application protocol, in step 316. In some embodiments, the user may set (select) the energy application protocol in response to the displayed initial state (e.g., the user may select a protocol from a plurality displayed protocols). The interface may send the energy application protocol to controller. An energy application protocol may include one or more rules at which energy may be applied to the energy application zone. The rules may include setting the amount of energy to be applied (e.g., temperature, power levels energy application durations) or the type of energy (e.g., RF energy, IR energy or convection heating) based on the received RF feedback. For example, when the RF feedback correlated with a processing state that indicates that yeast dough is fully proofed and ready to be baked, the controller may set a rule for an oven to apply 180° for 30 minutes. If the object is to be processed also by RF energy, the rules may control the selection of the excitation setups, from the plurality of excitation setups, at which RF energy may be applied. Additionally or alternatively, the rules may determine the amount of energy to be applied at each excitation setup, for example, by setting the amounts of power and/or time supplied to each radiating element (e.g., element 110, 120 and 130) from the RF energy source (e.g., source 112, 122 and 132). The energy application protocol may be set based on one or more RF feedbacks.

Energy may be applied to the energy application zone to process the object according to the energy application protocol set in step 316, in step 318. The energy may be applied via one or more heat sources (e.g., source 209, 209*a* and 209*b*). For example, source 209 may include a filament in a cooking oven, where the oven may include a thermostat and may be configured to heat the oven to 180° C. for 30 minutes. Additionally or alternatively, RF energy may be applied to process the object via radiating elements connected to one or more RF sources. The energy source and/or RF source may be controlled by the controller to apply the energy according to the set protocol. After or during the energy application, a second RF feedback (e.g., a computed RF feedback) may be received and optionally monitored (while processing the object) from the energy application zone to detect processing state(s) of the object after or during the energy application (step 320). In some embodiments, the processing state(s) may be displayed to the user (e.g., through an interface) during the processing. Optionally, the second type of RF feedback may be similar to the first type of RF feedback. Alternatively, the second type of RF feedback may be different from the first type of RF feedback. For example, the first computed RF feedback received in step 314 indicating that the yeast dough was fully proofed may include the DR, and the second computed RF feedback indicating that the yeast dough is fully baked may include a time derivative of the average DR. The values of the second RF feedback may be compared to a value available to the controller, e.g., a termination criterion, in step 322. The termination criterion may include at least one RF feedback value (e.g., a computed RF feedback value) correlated with a processing state of the object, e.g., the final desired state of the object. The termination criterion may be recorded and stored in: a memory associated with the controller, on a data indicative of instruction included in a machine readable element (e.g., a barcode tag or an RFID tag) or sent to the controller from a remote location connected to the controller (e.g., the Internet), in step 324. For example, the termination criterion may include a single value of the average DR, a set of values of DR(ESi), a set of values of $S_{11}$(ESi), a single value of DR at a particular excitation setup (ES), the time derivative of the power reflected from the zone, the time derivative of the DR(ESi) etc. If a value associated with the second RF feedback is substantially equal to the termination criterion, e.g., when the dough is completely baked, (step 322-YES), the energy may be terminated in step 326 and the processing of the object placed in the energy application zone may be ended. If the second RF feedback value is not equal to the termination criterion (step 322-NO), the process may return to step 314 and repeats until the termination criterion is met. In some embodiments, more than one termination criterion may be used in the RF energy application and the controller may cause application of the energy until all criteria are met, at least two criteria are met, etc.

In some embodiments, other criteria may be stored and compared during the RF energy application. For example, different criteria may be used to switch between various energy application protocols. A first protocol, for example, may apply 40° C. to proof a yeast dough, may be set according to RF feedback, set as a default or predetermined prior the RF energy application. The first protocol may be terminated when a first criterion, for example the criteria that the dough is fully proofed, may be met. The first protocol may be followed by a second EM application protocol (e.g., bake the dough at 180° C. for 30 minutes) and a second criterion (e.g., dough is baked), until a termination criterion may be applied. This concept is discussed broadly in reference to method 400.

Figure 3C:
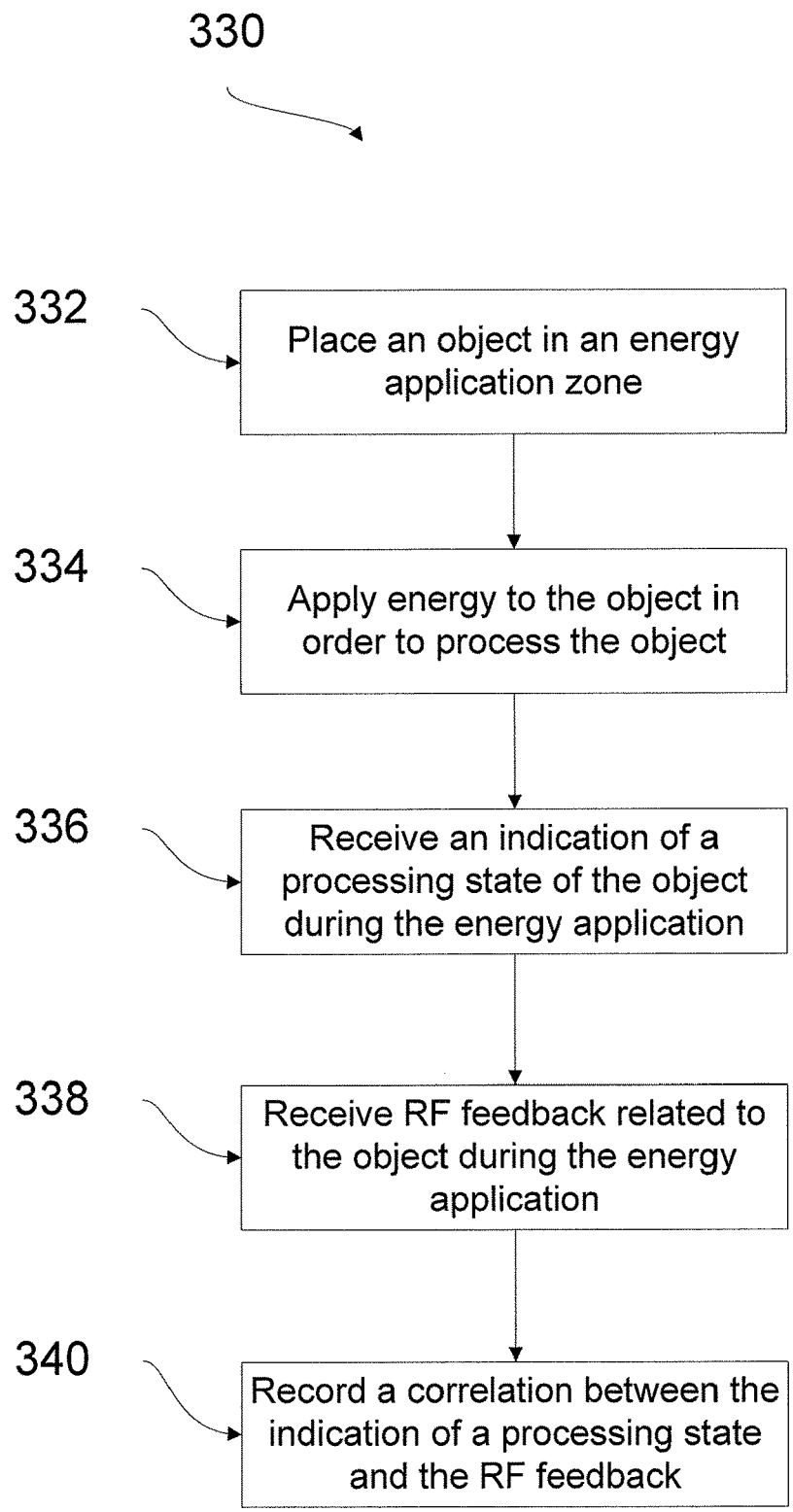
FIG. 3C includes a flowchart of a method for correlating and recording a processing state of an object with RF feedback, in accordance with some embodiments of the invention.

Method 330 for correlating and optionally recording a processing state of an object, indicated by at least one processing state indicator, with an RF feedback received during the processing of the object is presented in the flowchart in FIG. 3C, in accordance with some embodiments of the invention. Method 330 may be performed by controller 150, using apparatuses 100. An apparatus for recording a correlation of a processing state of an object, indicated or received by at least one processing state indicator, with RF feedback (e.g., one or more values or RF feedback or computed RF feedback) received from an energy application zone during processing of the object in the energy application zone may include one or more components discussed in reference to FIGS. 1A-1B and 2A-2B and may employ method 330. The apparatus may further be configured to create a machine readable element to be associated with an object. Method 330 may be performed on a test object, and the recorded correlation may be used to process similar or identical object. Method 330 may be performed in order to create a machine readable element or a processing program (e.g., cooking program) to be associated with objects similar or identical to the test object. An object to be processed may be placed in an energy application zone (e.g., zones 102 and cavities 200 and 210), in step 332. In some embodiments, the user may provide additional information regarding the test object—e.g., its type (for example: a cake, a steak etc.), size, position of the object in the cavity (e.g., a tray level in multi-level ovens). Alternatively or additionally, the additional information may be read from a machine readable element associated with the test object. Energy may be applied to the object to process the object, in step 334. For example, sources 209, 209a and/or 209b may apply convection heating to bake a cake placed in a cooking oven. In some embodiments, energy may be applied in accordance with instructions provided by the user (e.g., the user may indicate a desired amount of energy to be absorbed in the object (KJ) or may provide a desired temperature of a convection heating). An indication of a processing state (e.g., a chemical or physical property or a cooking state) of the object may be received during (i.e., before, during and after) the energy application, in step 336. The indication of the processing state of the object may be received from various processing state indicators, for example, sensors configured to sense a variable indicative of the processing state of the object placed in or around the energy application zone, e.g., sensors 140, 206 and 208. In some embodiments, the processing state sensed by the sensors (processing state indicators) may be displayed to a user. Additionally or alternatively, the indication of the processing state of the object may be received from a user and the processing state indicator may comprise a first user interface configured to receive from a user an indication of the processing state of the object (e.g., the degree of doneness, a desired color, etc.,). Controller 150 may record the indication of the processing state of the object. For example, the controller may record a temperature signal from a thermometer indicating the temperature inside a steak (e.g., when the steak's temperature has reached 50° C. and the steak reached a medium doneness level). In yet another example, the controller may record a weight, e.g., received from a scale, of berries placed in a drying cabinet to be dried. In some circumstances, the weight may indicate that the berries have lost a certain amount of water.

During the energy application and the processing (e.g., cooking, drying, baking etc.), RF feedback may be received from at least one detector configured to detect the RF feedback from the energy application zone (step 338). RF energy may be applied, optionally, by sweeping over a plurality of excitation setups (e.g., a plurality of frequencies) to the energy application zone. The RF energy may be emitted from the radiating elements (e.g., elements 110, 120, 130, 204a-204f and reflected back or coupled to the radiating elements. As a result of the RF energy application, an RF feedback may be received from the energy application zone and recorded (e.g, one or more values) by controller 150, during the processing of the object. For example, controller 150 may record the values of the DR at each excitation setup and/or the average DR over all excitation setups as a function of time. In some embodiments, the values of DR may be monitored during the some or all of the processing of the object. In some embodiments, the RF feedback received by the detector(s) and/or the computed RF feedback may be displayed to a user.

Figure 8A:
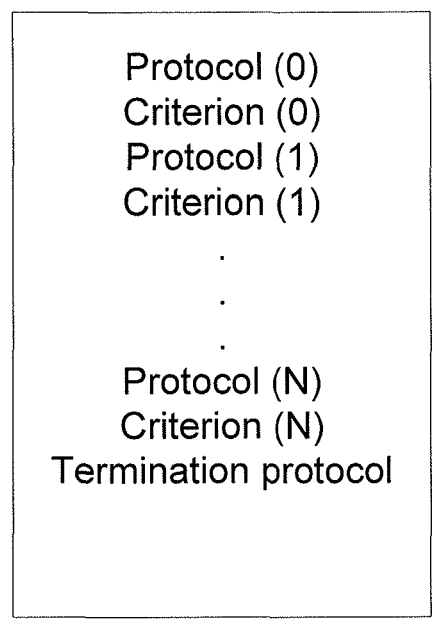
FIGS. 8A and 8B are representations of recordable elements in accordance with some embodiments of the invention.
Figure 8B:
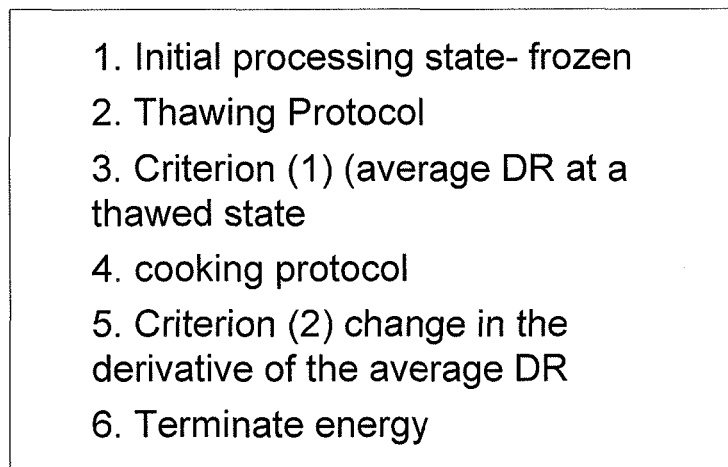

In some embodiments, the user may evaluate the process (e.g., the user may evaluate the processing state and compare this to a desired processing state). Optionally, when the desired results are not obtained—an additional test object may be processed with a different instructions—e.g., different energy protocols etc. In some embodiments, the user may indicate (e.g., via interface) that a desired results was obtained. Alternatively, an indication whether the desired result was obtained may be indicated by one or more sensors (processing state indicators) provided in the apparatus. In such case, the program (e.g., the one or more energy protocols) that was used for processing the object may be recorded on a machine readable element (for example: as illustrated in FIGS. 8A-8B). In some embodiments, the program may be displayed to a user for approval before recording it (e.g., on a machine readable element).

The RF feedback (e.g., one or more values or trends) may be correlated with the indication of object processing state (e.g., one or more signals received by processing state indicator) and the correlation may be recorded, in step 340. The controller may correlate the recorded indication of the processing state and the RF feedback as the feedback is obtained (at the same time, at different times, or at some later time). The recorded correlation(s) may be used to detect one or more processing states of the object and may set a criterion/criteria for controlling the energy application to process object(s) similar to the test object. For example, the temperature measurements of the object may be correlated to average DR values and the average DR correlated to a desired target temperature may be set as a criterion and may be recorded in a data storage portion included in machine readable element. In some embodiments, one or more of the RF feedback (e.g., values) may be correlated to at least one processing state of the object and may be recorded and stored in data indicative of instructions included in a machine readable element, and/or on a memory associated with the controller and/or in a remote location connected to the controller. In some embodiments, a machine readable element may be associated with an identification number (e/g/. tag ID) and the recorded data may be stored on a remote location such that the identification number may be associated with that data.

Figure 4:
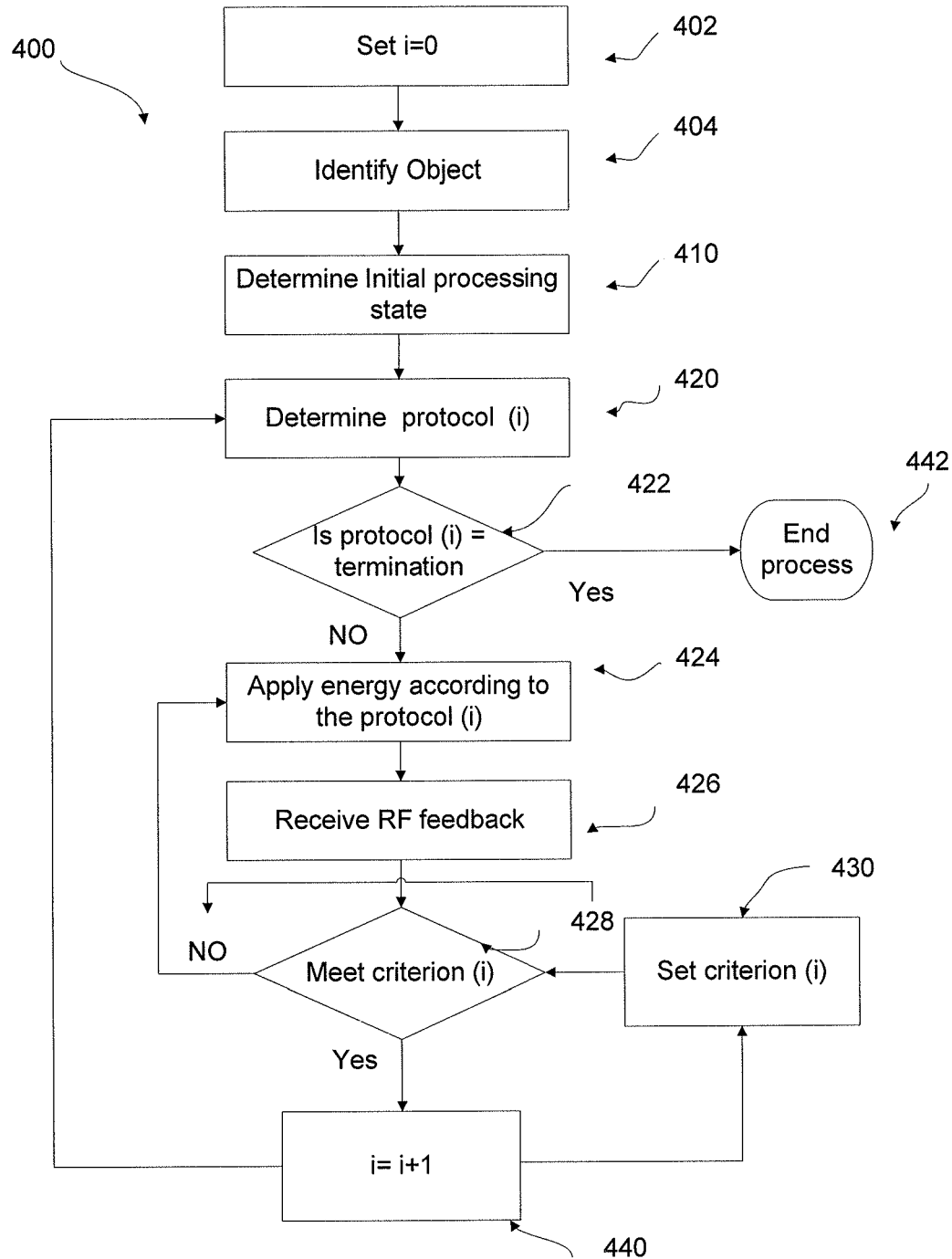
FIG. 4 includes a flowchart of a method for controlling energy application to process an object based on a criterion, in accordance with some embodiments of the invention.

FIG. 4 is a flowchart of a method 400 for controlling energy application based on a criterion, for example the criterion disclosed in step 340 of method 330, according to some embodiments of the invention. A controller (e.g., controller 150) may be configured to carry out method 400 utilizing any suitable system (e.g., apparatus 100). Method 400 may include switching between two or more energy protocols based on a detected criterion. The criterion may be associated with a processing state of the object or an associated RF feedback (e.g., computed RF feedback). The controller may determine an initial processing stage by setting i to zero (i=0), at step 402. Optionally, at the initial processing stage (i=0), the controller may identify the object to be processed based on identity information received from an interface, at step 404. An interface (e.g., interface 160) may include a system configured to read data recorded on a machine readable element, for example, a tag reader (e.g., a barcode reader or an RFID reader), and the identity of the object may be coded or recorded on the tag (e.g., a machine readable element such as a barcode, etc.). Additionally or alternatively, the identity of the object may be received from a user using any user interface 160 (e.g., GUI, touchpad, keypad, touch-screen etc.) configured to receive instruction(s) from a user and forward the instruction(s) to a controller. In some embodiments, the initial processing state of the object may be determined, in step 410. For example, the controller may determine the initial processing state of the object based on the identity of the object. The controller may correlate between the identity of the object and the initial processing state of the object. For example, the identity of the object may define the chemical composition and reaction mixture concentration in a solution introduced to a chemical reactor. In yet another example, the initial processing state may be recorded on a machine readable element associated with the object, and the controller may be configured to receive a data indicative of the initial processing state of the object (e.g., instructions) from the machine readable element. For example, a code printed on an instant cake powder package may identify the initial conditions of a cake powder mixture after adding the liquids (e.g., milk) and eggs at room temperature and after molding (in the cake mold) and made ready to be introduced to the cooking oven. In some embodiments the instructions recorded on the machine readable elements are further configured to cause the at least one controller (e.g., controller 150) to determine the initial condition of the object based on RF feedback received from the energy application zone. Alternatively, the initial processing state of the object (initial conditions) may be determined based on an RF feedback received from the energy application zone holding the object. In some embodiments, the initial conditions of the object may be determined by monitoring RF feedback. Value(s) of RF feedback received from the energy application zone (as a response to RF energy application) at the initial state of the object may be compared to RF feedback values recorded on a media accessible to the controller, for example a machine readable element, a memory associated with the controller, etc. The recorded RF feedback values may be correlated to at least one initial processing state of the object. A first protocol, comprising energy application parameters, may be determined in step 420. The first protocol may be determined based on the initial processing state of the object determined in step 410. For example, if the initial processing state of the object shows that the object is frozen, the determined first energy application protocol may comprise RF energy application parameters that may thaw the object, e.g., 'thawing script', for example using RF energy. Additionally, the initial processing state may indicate the temperature of the frozen object, and the first protocol may comprise energy application parameters for example, temperature and time in a convection oven. If the energy applied to process the object is RF energy—the protocol may include energy level, power level, time duration and/or selecting of one or more excitation setups from a plurality of excitation setups, and applying RF energy at the selected excitation setups, for thawing the object starting at the indicated temperature. Optionally, the first protocol (e.g., protocol (i)) may be determined based on data indicative of instructions recorded on a machine readable element or in a memory accessible to the controller. In some embodiments, the data indicative of instructions recorded on a machine readable element may include instructions configured to cause a controller to select the first protocol according to the initial processing state of the object or RF feedback received from the energy application zone. In some embodiments, one or more protocols may be included in data indicative of instructions recorded on the machine readable elements, and the controller may determine the protocol(i) from data recorded on the readable element. The data may include some or all of the energy application parameters and/or a code associated with some or all of the energy application parameters. The machine readable element or the memory may include processing instructions for processing the object. The instructions may include more than one protocol, and/or data related with the protocol, and/or data related with the initial processing state of the object. In some embodiments, when RF energy is further applied to process the object, the protocol may include a correlation between RF feedback values (e.g., computed RF feedback values) and the RF energy to be applied to the energy application zone. The correlation may be recorded on a readable element (e.g., bar-code), and all the other energy application parameters may be set regardless of the information in the machine readable element. For instance, the processing parameters included in the protocol (i) (e.g., the first protocol) may be set as a default of the processing apparatus, optionally the data indicative of instructions comprises an instruction to use the default protocol. The at least one correlation may be set such that the energy applied to the energy application zone may accelerate a chemical reaction in a chemical reactor. A different correlation may be set (e.g., recorded on a readable element) if the protocol is designed to puff un-puffed dough, taken from a refrigerator at 4° C. Other correlations can be set depending on the requirements of a particular application.

In step 422, the protocol is checked to determine whether the protocol is an energy application protocol or a termination protocol. An energy application protocol may be defined as any protocol that includes application parameters for controlling non-zero energy delivery to the energy application zone. A termination protocol may be defined a protocol involving application of zero energy to the energy application zone. If the protocol is a termination protocol (422: YES), the process ends (442). Otherwise, step 424 may be performed, and energy (e.g., RF energy, IR energy, convection heating energy, etc.) may be applied to the energy application zone according to protocol(i) (e.g., the first protocol) determined in step 420. For example, the protocol may include a correlation between a computed RF feedback and the RF energy to be applied to the energy application zone, and in performing step 424, the computed RF feedback may be calculated from one or more values of an RF feedback, and energy may be applied accordingly. In other embodiments, the protocol may include other energy application parameters.

In step 426, an RF feedback is received from the energy application zone, optionally in the presence of the object. The RF feedback may be monitored during energy application in accordance with protocol (i) (e.g., the first protocol). The feedback may include any RF feedback, either raw RF feedback parameters and/or computed RF feedback. For example, the feedback may include: the S parameters, DR, average DR, input impedance of radiating element(s), power detected in the energy application zone, their respective derivatives, averages, etc.

In step 428, the received RF feedback (e.g., its value(s)) may be checked (compared) against a criterion—criterion(i), e.g. to see if the criterion is met. The criterion may be or may be correlated to a processing state of the object. This step may be carried out during the energy application or in an intermission in energy application. Meeting the criterion may be checked continuously during the energy application, or intermittently, e.g. periodically, for example, every 1 sec or 5 sec or 10 sec, etc. Additionally or alternatively, the RF feedback may be checked against the criterion upon occurrence of certain events. For example, the RF feedback may be compared to the criterion when an indication indicative of the object's temperature shows a temperature change larger than 1° C., when an indication indicative of the object's humidity changes by a predetermined amount, every predetermined number of sweeps, etc. The criterion may include one or more RF feedback (e.g., values) correlated with at least one processing state of the object. The criterion may be set according to method 330, disclosed in the flowchart at FIG. 3C. The criterion may be recorded on a data storage portion in a machine readable element, on a memory associated with the controller or on a remotely located media accessible to the controller. The controller may receive the criterion from the machine readable element and/or the memory and/or the media.

In step 428, the controller may determine if the RF feedback (e.g., its value) meets the criterion. In case the feedback does not meet the criterion yet (step 426:NO), Energy application may continue using the same protocol determined in step 420 during an (i) time period (e.g., a first time period) before RF feedback received from the energy application zone meets a criterion. Steps 422, 424, 426, and 428 may be repeated until the criterion is met (Step 428: YES). When criterion(i) is met, another criterion may be defined in step 430 and i may be set to i=i+1 (step 440). After the criterion is met protocol(i+1) (e.g., a second protocol) may be determined, step 420 may be repeated, and the energy may be applied to the energy application zone according to the protocol(i+1) during a second time period after RF feedback received from the energy application zone meets criterion(i) (repeating step 424).

Cooking experiments for correlating a cooking state of a food item with an RF feedback were conducted in an experimental cooking oven. The cooking oven included similar components as disclosed in FIGS. 1B and 2A: a controller, a convection heat source, two radiating elements each contacted to an RF source and a detector, and a temperature sensor. In the first experiment, a ready-to-bake frozen pizza was defrosted and cooked by applying convection heating at 180° C. The temperature of the pizza and the average DR were detected and monitored as function of the cooking time. A sharp change in the slope (the time derivative) of the average DR was detected when the pizza was thawed and a change in the sign of the time derivative (from positive to negative) was observed when the pizza was fully backed.

Figure 5:
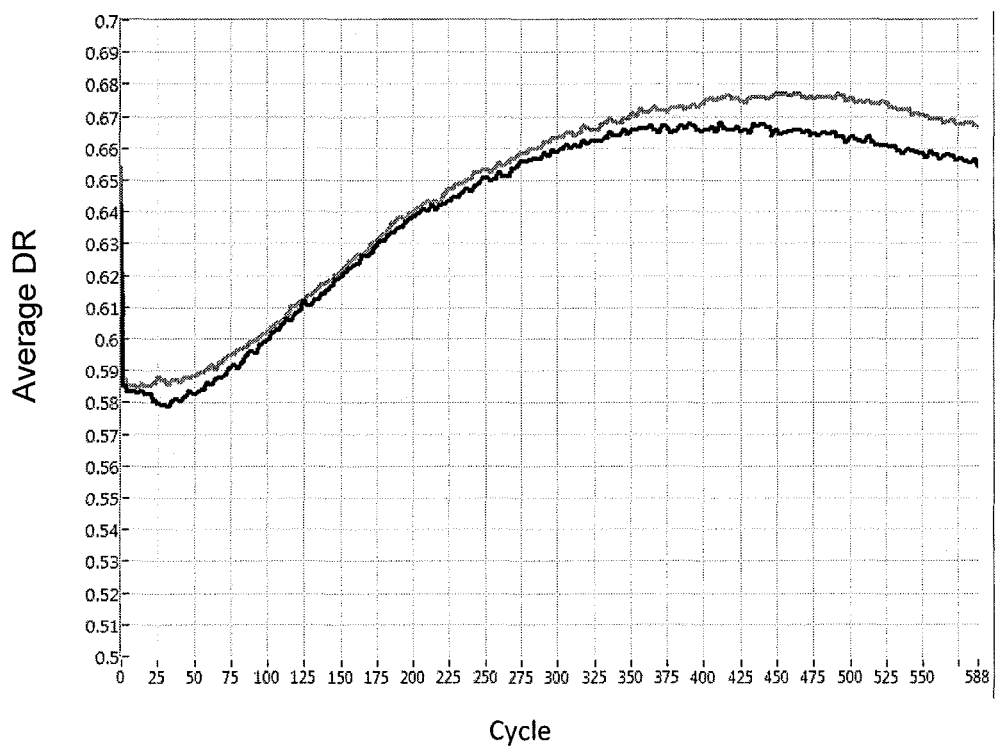
FIG. 5 includes a graphical representation of results obtained in a cooking experiment for correlating RF feedback (average DR) with cooking states of a vanilla cake according to some embodiments of the invention.

FIG. 5 presents two measurements of the average DR (an example of a computed RF feedback) taken from two different radiating elements, during baking experiments of a vanilla cake. An instant vanilla cake mixture was prepared according to the instructions on the mixture package and placed in the same experimental cooking oven used to bake the pizza. The oven was heated to 180° C. The average DR was monitored by the controller every 3 seconds, and the baking state of the cake was monitored visually by a chef periodically. The entire baking time was approximately 30 minutes. The x axis in FIG. 5 is the number of the average DR detection cycles taken every 3 seconds. At the first 350 cycles (17.5 minutes) the average DR increased with time and has a positive time derivative. From approximately 350 to 500 cycles (25 minutes from the beginning of baking) the average DR did not change significantly (the time derivative is approximately zero). At the end of baking, the value of DR decreases in time (i.e., a negative time derivative), indicating that the cake is ready. Similar results were obtained in cooking apple pie.

Figure 6A:
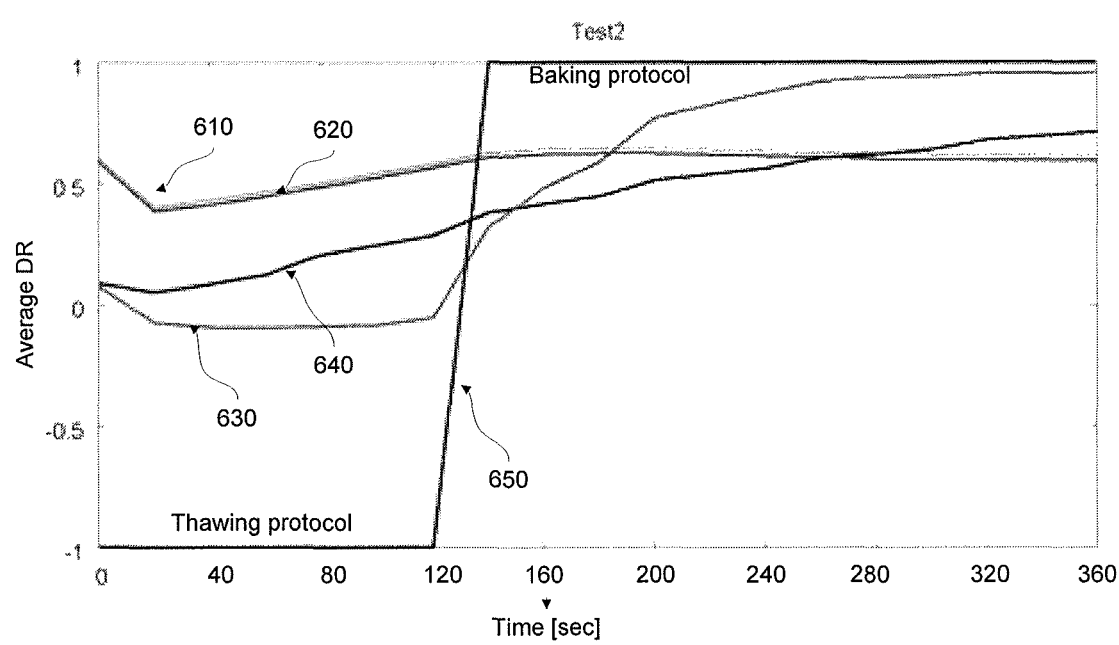
FIG. 6A presents results from pizza thawing and baking experiments, in accordance with some embodiments of the invention.
Figure 6B:
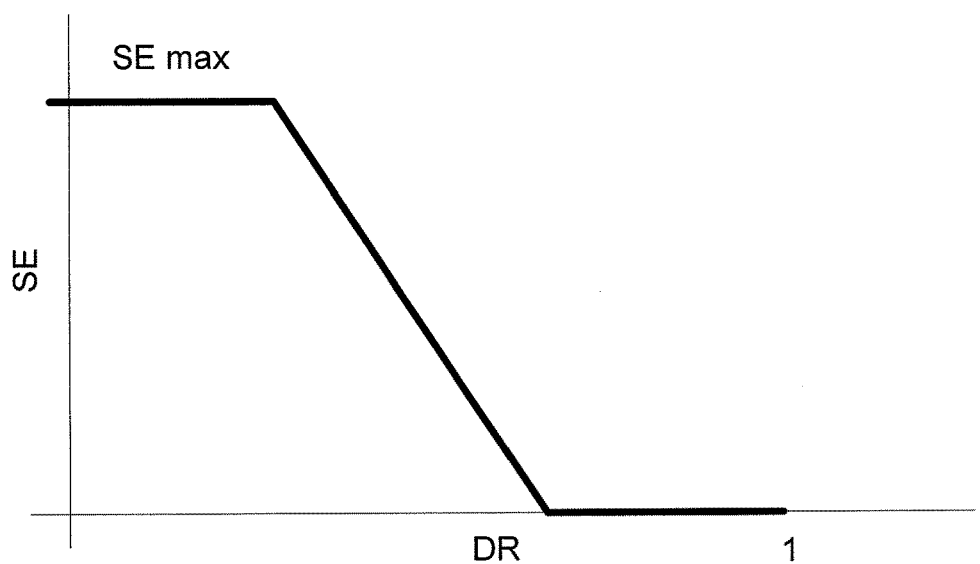
FIG. 6B represents a thawing protocol used in a thawing experiment in accordance with some embodiments of the invention.
Figure 6C:
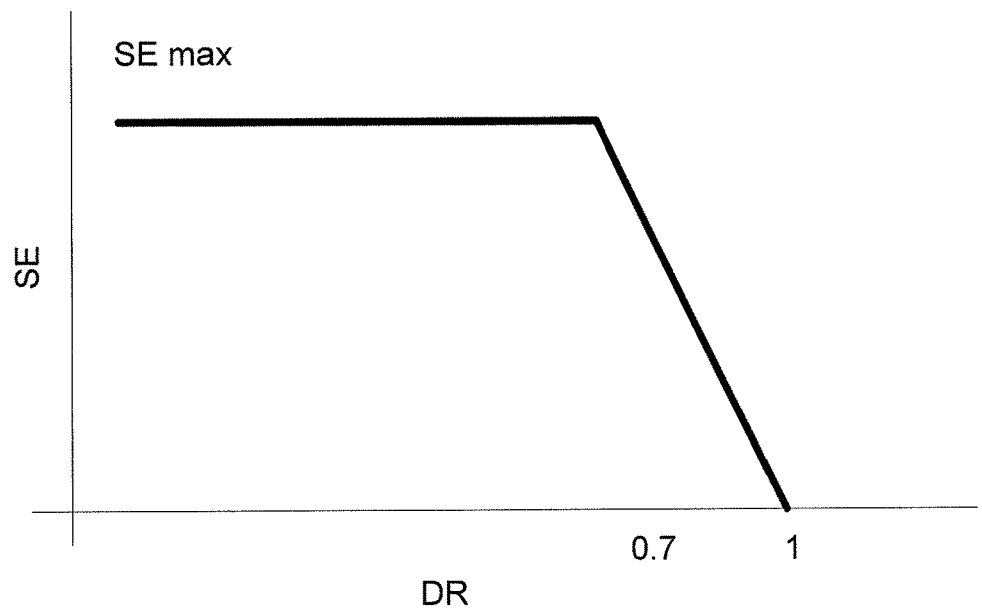
FIG. 6C represents a baking protocol used in a baking experiment in accordance with some embodiments of the invention.

Another baking experiment using a frozen pizza was conducted using apparatus and methods according to some embodiments of the invention. The baking experiments were performed in an experimental RF cooking oven (an oven that employs RF energy for processing, e.g., cooking, food objects) comprising two radiating elements. A frozen ready-to-bake pizza at a temperature of −18° C. (deepfreeze) weighing 500 grams and having a diameter of 30 cm was placed in the experimental RF cooking oven. During the baking experiment, an RF feedback of the average DR (i.e., a computed RF feedback) was monitored together with the temperature (i.e., an indication for the processing state) of the pizza at two locations, one in the center and the other at the edge of the pizza. The results of the monitored average DR and the monitored temperature are presented in the graphs of FIG. 6A. The temperature divided by 100 (i.e. T[° C.]/100) in the center of the pizza is presented in graph 630, and the temperature divided by 100 at the edge of the pizza is presented in graph 640. The average DR measured and calculated for the first and second radiating elements are presented in graphs 610 and 620. The RF energy application protocols are illustrated as line 650. A first protocol was chosen to be a "thawing protocol" based on the initial processing state of the pizza. The protocol parameters for applying RF energy were: using frequencies between 800-1000 MHz, supplying energy (SE) to the radiating elements of the RF cooking oven as a function of the DR at each frequency, according to the thawing protocol presented in FIG. 6B. No energy was applied to frequencies associated with a DR higher than 0.7. Monitoring the temperature showed thawing (i.e., a processing state of the object) of the edge part of the pizza after 20 sec and the inner part of the pizza after 120 sec. Monitoring the average DR, and in particular the time derivative of the average DR, showed a change in the slope of the average DR from positive (dDR/dt=positive number) to a small negative or almost no slope (dDR/dt=approximately 0) after the pizza was thawed (e.g., phase change). The change in the derivative of the average DR may be correlated to a "thawing state" and may be used as a criterion for changing from thawing protocol to baking protocol. After 120 sec of applying a 'thawing protocol', a 'baking protocol' was applied using frequencies between 800-1000 MHz, supplying energy to the radiating elements as function of the DR(f) (the dissipation ratio as a function of the frequency) according to the protocol presented in FIG. 6C. The maximum available energy was applied at all frequencies associated with a DR lower than 0.7, and a linear correlation between the DR and SE were applied at frequencies associated with DR higher than 0.7. The end of baking was indicated by a user (e.g., a chef) based on the color of the topping cheese (i.e., a processing state of the pizza), which became slightly brown when the average DR reached a value of 0.6. The average DR value of 0.6 may be correlated to an end of baking state of a pizza and may be used as a criterion for terminating the RF energy application when the pizza is fully cooked.

Figure 7:
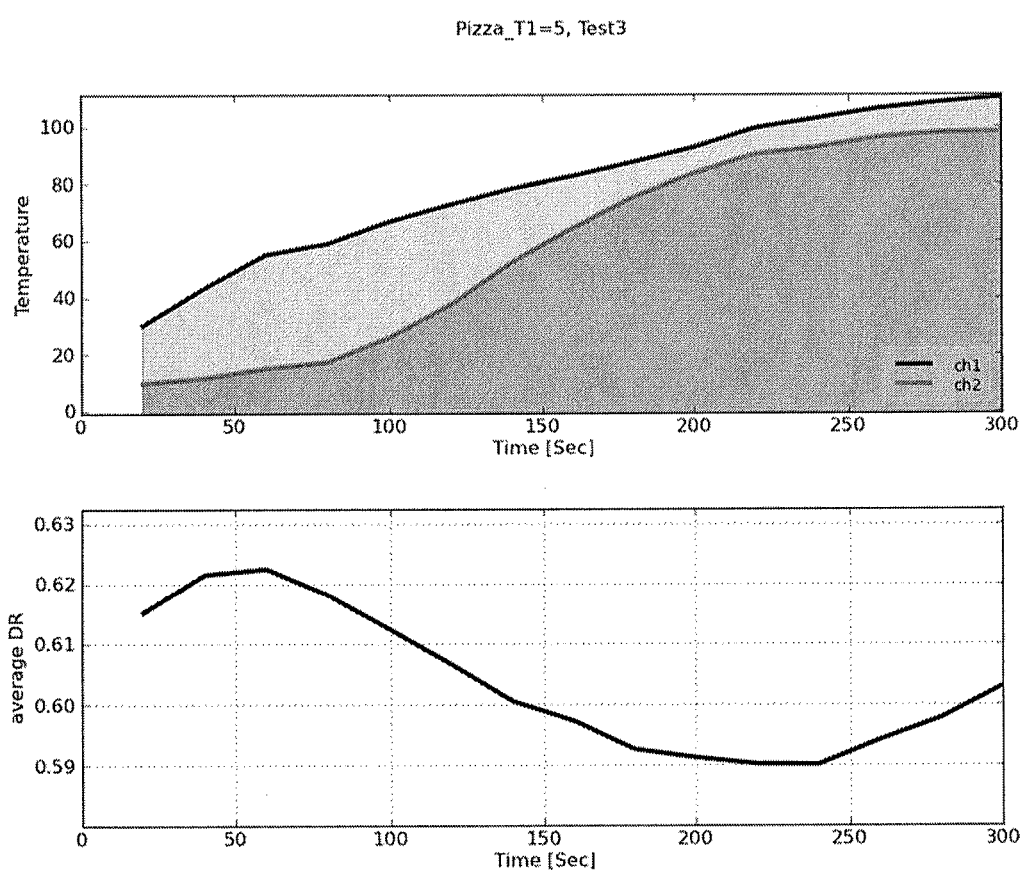
FIG. 7 presents results from pizza baking experiments in accordance with some embodiments of the invention.

In another baking experiment, a thawed, unbaked pizza weighing 500 grams and having a diameter of 30 cm at room temperature was placed in an experimental RF cooking oven. During the baking experiment, an RF feedback of the average DR was monitored together with the temperature of the pizza at two locations, one in the center (denoted as ch2) and the other at the edge of the pizza (denoted as ch1). The results of the monitored average DR and the monitored temperature are presented in the graphs of FIG. 7. The pizza was indicated as being ready and fully baked when the temperature exceeded 85 [deg] C., after approximately 240 sec. The average DR started to rise after 240 sec, and the derivative of the average DR changed from negative to positive. The change in the derivative may be correlated with the baking state of the pizza and may be used as a criterion for applying the RF energy termination protocol.

FIGS. 8A and 8B are illustrations representing two optional machine readable elements comprising a data indicative of instructions (the instructions being configured to cause the at least one controller to control the energy application to process the object) recorded on each element, in accordance with some embodiments of the invention. In FIG. 8A illustrates a general data indicative of instructions that includes various protocols (e.g., at least a first protocol and a second protocol) and criteria. FIG. 8B includes an exemplary recorded element with data indicative of instructions for preparing a pizza. The instructions may include a step for determining the initial processing state of the pizza and a thawing protocol (for example, a protocol presented in FIG. 6B) if the pizza is frozen. The instructions may further include a criterion for determining if the pizza is thawed and a cooking protocol (for example, a protocol presented in FIG. 6C) for cooking the pizza. The instructions may include a criterion for determining if the pizza is ready, such as, for example, a change in the derivative of the average DR, as disclosed with respect to FIG. 7. The instructions may also include a termination protocol.

As used herein, if a machine (e.g., a controller) is described as configured to perform a task (e.g., configured to cause application of a predetermined field pattern), then, in some embodiments, the machine performs this task during operation. Similarly, when a task is described as being done in order to establish a target result (e.g., in order to apply a plurality of EM field patterns to the object), then, in some embodiments, carrying out the task may accomplish the target result. As used herein, the term predetermined means only that the associated quantity or value is calculated or otherwise determined beforehand. Predetermined values may include values stored in memory; values calculated, observed, measured, read into, received, etc. before commencement of EM energy processing; or any values calculated, observed, measured, read into, received, etc. during such processing.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate embodiment of the invention.

Moreover, it will be apparent to those skilled in the art from consideration of the specification and practice of the present disclosure that various modifications and variations can be made to the disclosed systems and methods without departing from the scope of the invention, as claimed. For example, one or more steps of a method and/or one or more components of an apparatus or a device may be omitted, changed, or substituted without departing from the scope of the invention. Thus, it is intended that the specification and examples be considered as exemplary only, with a true scope of the present disclosure being indicated by the following claims and their equivalents.

What is claimed is:

1. A method for applying RF energy to determine a processing state of an object placed in a cavity having an energy application zone, during processing of the object, the method comprising:
    applying RF energy to the object during the processing via at least one radiating element;
    receiving RF feedback from at least one detector connected to the at least one radiating element, said RF feedback being indicative of a dielectric response of the cavity and/or the object to electromagnetic (EM) fields excited in the cavity;
    mathematically manipulating the RF feedback to obtain computed RF feedback;
    determining one or more processing states of the object based on a correlation between the computed RF feedback and the one or more processing states of the object; and
    monitoring the computed RF feedback during the applying to monitor the one or more processing states of the object.

2. The method of claim 1, wherein the computed RF feedback comprises one or more results of mathematical manipulation on two or more directly measurable values of the RF feedback.

3. The method according to claim 1, further comprising receiving the correlation between the computed RF feedback and the one or more processing states of the object.

4. The method according to claim 3, further comprising receiving the correlation between the computed RF feedback and the one or more processing states of the object from a memory associated with a controller.

5. The method of claim 4, wherein the controller is configured to cause the applying.

6. The method according to claim 3, further comprising receiving the correlation between the computed RF feedback and the one or more processing states of the object from a machine readable element associated with the object, and using the correlation to determine the one or more processing states of the object.

7. The method according to claim 1, wherein the processing of the object includes applying heat to the object.

8. The method according to claim 7, wherein the applying heat includes applying RF energy to heat the object.

9. The method of claim 8, wherein the applying RF energy includes applying RF energy to heat the object at a first power level and applying RF energy to receive the computed RF feedback at a second power level, the first power level is higher than the second power level.

10. The method of claim 8, wherein the applying RF energy includes applying RF energy to heat the object at a first average amount of energy per excitation setup and applying RF energy to receive the computed RF feedback at a second average amount of energy per excitation setup, the first average amount of energy per excitation setup is higher than the second average amount of energy per excitation setup.

11. The method of claim 1, wherein the computed RF feedback includes results of mathematical manipulation of at least two of reflected energy, coupled energy, incident energy, S parameters, or input impedance.

12. The method of claim 1, wherein the one or more processing states of the object is a phase of the object.

13. The method of claim 1, wherein the one or more processing states of the object is a flow rate of the object.

14. The method of claim 1, wherein the one or more processing states of the object is a pH of the object.

15. The method of claim 1, wherein the object is a food item and the one or more processing states of the object include cooking states.

16. The method of claim 1, further comprising controlling the applying based on the one or more determined processing states of the object.

17. The method of claim 1, wherein the computed RF feedback includes an indication of EM energy absorbability of the object.

18. The method of claim 1, further comprising terminating the processing of the object when the one or more processing states of the object reach a target value.

19. An apparatus for applying RF energy, via at least one radiating element, to determine a processing state of an object placed in a cavity, during processing of the object, the apparatus comprising:
an RF energy application unit configured to apply energy, via the at least one radiating element, to the object in an energy application zone in order to generate RF feedback;
at least one detector connected to the at least one radiating element, said at least one detector being utilized to detect RF feedback indicative of a dielectric response of the cavity and/or the object to electromagnetic (EM) fields excited in the cavity; and
at least one processor configured to:
cause RF energy application by the RF energy application unit;
receive RF feedback from the at least one detector, said RF feedback being indicative of a dielectric response of the cavity and/or the object to electromagnetic (EM) fields excited in the cavity;
mathematically manipulate the received RF feedback to obtain computed RF feedback;
determine one or more processing states of the object based on a correlation between the computed RF feedback and the one or more processing states of the object; and
monitor the computed RF feedback during the processing, to monitor the one or more processing states of the object.

20. The apparatus of claim 19, wherein the at least one processor is further configured to cause application of energy to process the object.

21. The apparatus according to claim 19, wherein the at least one detector is configured to detect directly measurable values of the RF feedback, and wherein the processor is configured to calculate the computed RF feedback based on one or more of the directly measurable values of the RF feedback, and wherein the RF feedback correlated with the one or more processing states of the object is the computed RF feedback.

22. The apparatus according to claim 21, wherein the computed RF feedback includes an indication of EM energy absorbability of the object.

23. The apparatus according to claim 21, wherein the computed RF feedback includes results of mathematical manipulation of at least two of reflected energy, coupled energy, incident energy, S parameters or input impedance.

24. The apparatus according claim 19, wherein the processor is configured to cause application of the RF energy at a plurality of frequency-phase combinations.

25. The apparatus according to claim 19, further comprising at least one heat source to apply heat to process the object.

26. The apparatus according claim 19, wherein the object includes a food item and the one or more processing states include cooking states.

27. The apparatus according to claim 19, wherein the at least one processor is further configured to control the processing based on the determined one or more processing states.

28. The apparatus according to claim 27, wherein the control includes terminating the processing when the one or more processing states reaches a target value.

29. The apparatus according to claim 19, further comprising an interface configured to receive information.

30. The apparatus of claim 29, wherein the information includes an indication of the one or more processing states of the object.

31. The apparatus of claim 29, wherein the information includes at least one energy application protocol.

32. The apparatus according to claim 29, wherein the information is recorded on a machine readable element and the interface is configured to read the information from the machine readable element.

33. A method for processing an object placed in an energy application zone comprising:
applying RF energy, via at least one radiating element, to the object in the energy application zone;
receiving by a processor RF feedback from a sensor located in or around the energy application zone, said RF feedback being indicative of a dielectric response of the cavity and/or object to electromagnetic (EM) fields excited in the cavity;

mathematically manipulating the received RF feedback to obtain computed RF feedback;

monitoring the computed RF feedback during the applying to monitor the processing state of the object based on a correlation between the computed RF feedback and one or more processing states of the object; and terminating the applying when the computed RF feedback reaches a target value.

34. The method of claim 33, wherein the processing of the object includes applying heat to heat the object.

35. The method of claim 33, wherein the computed RF feedback includes results of mathematical manipulation of at least two of reflected energy, coupled energy, incident energy, S parameters, or input impedance.

* * * * *